US012104995B2

(12) United States Patent
Wu

(10) Patent No.: US 12,104,995 B2
(45) Date of Patent: Oct. 1, 2024

(54) SYSTEMS AND METHODS FOR PERFORMING A REAL-TIME ASSAY OF A SAMPLE

(71) Applicant: AMGEN INC., Thousand Oaks, CA (US)

(72) Inventor: Chao-Hsiang Wu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 891 days.

(21) Appl. No.: 16/635,941

(22) PCT Filed: Aug. 1, 2018

(86) PCT No.: PCT/US2018/044887
§ 371 (c)(1),
(2) Date: Jan. 31, 2020

(87) PCT Pub. No.: WO2019/028187
PCT Pub. Date: Feb. 7, 2019

(65) Prior Publication Data
US 2020/0355582 A1   Nov. 12, 2020

Related U.S. Application Data

(60) Provisional application No. 62/539,803, filed on Aug. 1, 2017.

(51) Int. Cl.
*G01N 1/34* (2006.01)
*G01N 33/68* (2006.01)
*G01N 1/38* (2006.01)

(52) U.S. Cl.
CPC .......... *G01N 1/34* (2013.01); *G01N 33/6848* (2013.01); *G01N 2001/385* (2013.01)

(58) Field of Classification Search
CPC .......................... G01N 1/34; G01N 33/6848
See application file for complete search history.

(56) References Cited

U.S. PATENT DOCUMENTS 6,344,172 B1 * 2/2002 Afeyan .............. B01D 15/1871
422/527
6,887,429 B1 * 5/2005 Marshall ............ G01N 35/1097
422/50

(Continued)

FOREIGN PATENT DOCUMENTS

WO        9631782 A1     10/1996
WO     WO 96/31782   * 10/1996
(Continued)

OTHER PUBLICATIONS

Automated Analytical System for the Examination of Protein Primary Structure Y.L. Frank Hsieh, HongQi Wang, Chris Elicone, Jonathan Mark, Stephen A. Martin, Fred Regnier Anal. Chem. 1996, 68, 455-462 (Year: 1996).*

(Continued)

*Primary Examiner* — Brian R Gordon
*Assistant Examiner* — Dwan A Gerido
(74) *Attorney, Agent, or Firm* — Melissa E. Karabinis

(57) ABSTRACT

Systems, and methods that facilitate the performance of an assay of a sample substantially in real-time. Thus, the assay can be performed, and the desired result obtained, much more quickly than allowed by conventional systems and methods.

6 Claims, 4 Drawing Sheets

Specification includes a Sequence Listing.

(56) References Cited

U.S. PATENT DOCUMENTS

| | | | |
|---|---|---|---|
| 9,322,014 B1* | 4/2016 | VanderNoot | ....... G01N 30/6043 |
| 2004/0009567 A1 | 1/2004 | Duewel et al. | |
| 2004/0009597 A1 | 1/2004 | Duewel et al. | |
| 2004/0053356 A1 | 3/2004 | Duewel et al. | |
| 2013/0171658 A1 | 7/2013 | Fulton | |
| 2014/0030732 A1 | 1/2014 | Staples | |
| 2020/0355582 A1 | 11/2020 | Wu et al. | |
| 2022/0137061 A1 | 5/2022 | Wu et al. | |

FOREIGN PATENT DOCUMENTS

| | | |
|---|---|---|
| WO | WO-2009/027041 A1 | 3/2009 |
| WO | WO-2012/037407 A1 | 3/2012 |

OTHER PUBLICATIONS

Ündey et al., "Applied advanced process analytics in biopharmaceutical manufacturing: Challenges and prospects in real-time monitoring and control," *Journal of Process Control* 20:1009-1018 (2010).

MX 202000248 Search Report, May 17, 2022 (3 pages).

CL 202000248 Office Action dated Sep. 7, 2021.

PCT/US2018/0444887 International Search Report.

Hsieh Y.L.F., et al., Automated Analytical System for the Examination of Protein Primary Structure, Analytical Chemistry, Feb. 1, 1996, American Chemical Society, US.

Dong, et al, High-Throughput, Automated Protein A Purification Platform with Multiattribute LC-MS Analysis for Advanced Cell Culture Process Monitoring, Analytical Chemistry, Sep. 6, 2016, American Chemical Society, Epub Aug. 23, 2016, US.

Amand et al., Development of at-line assay to monitor charge variants of MAbs during production, Biotechnology Progress, Jan. 1, 2014, American Chemical Society, Jan. 1, 2014.

Pais, et al, Towards real-time monitoring of therapeutic protein quality in mammalian cell processes, Current Opinion in Biotechnology, Jul. 16, 2014, Elsevier Ltd, Jul. 16, 2014.

Nadja, et al. Determination of critical quality attributes for monoclonal antibodies using quality by design principles, Biologicals., Jul. 25, 2016, Academic Press Ltd, Jul. 25, 2016, GB.

International Search Report and Written Opinion received for PCT/US2018/044887 dated Oct. 15, 2018.

Dong et al., "High-Throughput, Automated Protein A Purification Platform with Multiattribute LC-MS Analysis for Advanced Cell Culture Process Monitoring," Analytical Chemistry. 7 pages. Aug. 23, 2016.

Amand et al., "Development of at-line assay to monitor charge variants of MAbs during production," Biotechnology Progress, 7 pages. Dec. 30, 2013.

Pais et al., "Towards real-time monitoring of therapeutic protein quality in mammalian cell processes," Current Opinion in Biotechnology. 7 pages. Jul. 16, 2014.

Nadja et al., "Determination of critical quality attributes for monoclonal antibodies using quality by design principles," Biologicals, Academic Press Ltd. 15 pages. Jul. 25, 2016.

Hsieh et al., "Automated Analytical System for the Examination of Protein Primary Structure," Analytical Chemistry, American Chemical Society. 8 pages. Feb. 1, 1996.

Tharmala et al., "A Framework for Real-Time Glycosylation Monitoring (RT-GM) in Mammalian Cell Culture," Biotechnology and Engineering, 9 pages. Jun. 2015.

International Search Report and Written Opinion received for PCT/US2018/044891, dated Oct. 16, 2018.

Huhn et al., "IgG glycosylation analysis," Proteomics, 32 pages. Feb. 1, 2009.

Alt, et al., Determination of critical quality attributes for monoclonal antibodies using quality by design principles, Science Direct, Biologicals, Jun. 9, 2016.

Chinese Patent Application 2018800462384, Office Action (Jan. 20, 2023).

International Search Report and Written Opinion Received for PCT/US2018/044891 (Oct. 16, 2018).

CN Application 2018800469557, Office Action (Apr. 1, 2023).

* cited by examiner

SYSTEMS AND METHODS FOR PERFORMING A REAL-TIME ASSAY OF A SAMPLE

CROSS-REFERENCE TO RELATED APPLICATION

The present application claims the priority benefit of U.S. Provisional Patent Application No. 62/539,803, entitled "Systems and Methods for Performing a Real-Time Assay of a Sample" and filed Aug. 1, 2017, the entire disclosure of which is hereby incorporated by reference herein.

FIELD OF THE DISCLOSURE

The present disclosure relates generally to assays and, more specifically, to performing a real-time assay of a sample.

SEQUENCE LISTING

The present application is being filed with a sequence listing in electronic format. The sequence listing provided as a file titled, "51800_Seqlisting.txt" created Jul. 31, 2018 and is 263,964 bytes in size. The information in the electronic format of the sequence listing is incorporated herein by reference in its entirety.

BACKGROUND

Assays are commonly performed to quantify one or more attributes of an analyte such as a drug, a biochemical substance, or a cell. An example of such an assay is the multi-attribute method (MAM) assay, which can detect and quantify Critical Quality Attributes (CQAs), identified by the Quality Target Product Profile (QTPP), of a sample (Development of a quantitative mass spectrometry multi-attribute method for characterization, quality control testing and disposition of biologics. Rogers R S, Nightlinger N S, Livingston B, Campbell P, Bailey R, Balland A. *MAbs*. 2015; 7(5): 881-90). The MAM assay is a manually-operated process that is performed in, for example, a Large Molecule Release Testing (LMRT) laboratory. MAM is a liquid chromatography (LC)-mass spectrometry (MS)-based peptide mapping method, comprising three steps: (1) sample preparation (such as polypeptide denaturation, reduction, alkylation, and digestion; (2) separation of the digested polypeptides by LC and detection by MS; and (3) analysis of the data for targeted CQAs and detection of new signal (i.e., peaks) when compared to a reference standard.

CQAs are chemical, physical, or biological properties that are present within a specific value or range values. For example, for large polypeptide therapeutic molecules, physical attributes and modifications of amino acids (the building blocks of polypeptides) are important CQAs that are monitored during and after manufacturing, as well as during drug development. Unlike conventional analytical assays that track changes in peak size and peak shape of whole or partial polypeptides, MAM detects specific CQAs at the amino acid level.

However, while MAM is an important advance in the assessment of CQAs of polypeptide therapeutic molecules during development, manufacturing, and storage (assessing, e.g., stability), analysis can consume seven to ten days, from sample preparation to final analysis, time that drives costs and delays development and drug release. For example, polypeptide therapeutics are customarily produced by cultured cells expressing the target polypeptide. Such production systems are not easily "put on hold" while MAM analysis of CQAs is pending, resulting in the cells producing the target polypeptide with CQAs that do not meet specifications—a waste of time, materials, and manpower. Furthermore, delays of seven to ten days accumulate during drug development, for example, when optimizing culture conditions, impeding delivery of important and new polypeptide pharmaceuticals to patients. Thus, there is a need for efficient and faster methods to facilitate CQA analysis using MAM.

SUMMARY

One aspect of the present disclosure provides a method for performing a real-time assay. The method includes the steps of: (a) moving a sample of a product containing polypeptides to a polypeptide-binding column via a first holding coil; (b) binding the polypeptides in the sample to the polypeptide binding column, thereby separating the polypeptides in the sample from a remainder of the sample; (c) moving an elution buffer solution from a buffer source to the polypeptide binding column, via the first holding coil, and through a second holding coil downstream of the polypeptide binding column, thereby eluting polypeptides bound to the polypeptide binding column and moving an elution/polypeptide mixture comprising the elution buffer solution and the eluted polypeptides to the second holding coil; (d) moving the elution/polypeptide mixture from the second holding coil to a reaction chamber; (e) incubating the polypeptides in the elution/polypeptide mixture in the reaction chamber, resulting in denatured polypeptides; (f) moving a reducing reagent that cleaves disulfide bond cros slinks to the reaction chamber via the first holding coil after (e); (g) incubating the denatured polypeptides with the reducing reagent in the reaction chamber, resulting in denatured and reduced polypeptides; (h) moving an alkylating reagent that alkylates sulfhydryls to the reaction chamber after (g); (i) incubating the denatured and reduced polypeptides with the alkylating reagent in the reaction chamber, thereby alkylating the denatured and reduced polypeptides; (j) moving the denatured, reduced, and alkylated polypeptides, the elution buffer solution, the reducing reagent, and the alkylating reagent from the reaction chamber to a desalting column via the first holding coil, the desalting column equilibrated with a proteolysis buffer; (k) applying the denatured, reduced, and alkylated polypeptides to the desalting column, thereby separating the denatured, reduced, and alkylated polypeptides from the reducing and alkylating reagents, and resulting in desalted polypeptides; (l) moving the desalted polypeptides to a proteolytic enzyme column downstream of the desalting column; (m) digesting the desalted polypeptides in the third polypeptide column, resulting in digested polypeptides; and (n) moving the digested polypeptides to an analytical device for analysis of the digested polypeptides.

Another aspect of the present disclosure provides a method for performing a real-time assay using a closed system including a multi-port valve, a first holding coil upstream of the multi-port valve, a polypeptide binding column fluidly coupled to and downstream of a first port of the multi-port valve, a second holding coil fluidly coupled to and downstream of the polypeptide binding column, a reaction chamber fluidly coupled to and downstream of second and third ports of the multi-port valve, a desalting column fluidly coupled to and downstream of a fourth port of the multi-port valve, and a proteolytic enzyme column downstream of the desalting column. The method includes:

(a) moving, via a controller communicatively coupled to the closed system, a sample of a product containing polypeptides to the first holding coil; (b) positioning, via the controller, the multi-port valve in a first position in which the first holding coil is connected to the polypeptide binding column via the first port of the multi-port valve, such that the sample flows to the first column, whereby polypeptides in the sample bind to the polypeptide binding column; (c) when the multi-port valve is in the first position, moving, via the controller, an elution buffer solution from a source of elution buffer solution to the second holding coil via the polypeptide binding column, such that the elution buffer solution elutes substantially all of the polypeptides bound to the polypeptide binding column; (d) moving, via the controller, the multi-port valve to a second position in which the second holding coil is connected to the reaction chamber via the second port of the multi-port valve; (e) when the multi-port valve is in the second position, moving, via the controller, an elution/polypeptide mixture comprising the elution buffer solution and the eluted polypeptides to the reaction chamber, whereby the polypeptides in the elution/polypeptide mixture are denatured; (f) moving, via the controller, the multi-port valve to a third position in which the first holding coil is connected to the reaction chamber via the third port of the multi-port valve; (g) after (f), moving, via the controller, a reducing reagent that cleaves disulfide bond crosslinks to the first holding coil, and moving, via the controller, the reducing reagent from the first holding coil to the reaction chamber via the third port of the multi-port valve, thereby reducing the denatured polypeptides; (h) after (g), moving, via the controller, an alkylating reagent that alkylates sulfhydryl groups to the first holding coil, and moving, via the controller, the alkylating reagent from the first holding coil to the reaction chamber via the third port, thereby alkylating the denatured and reduced polypeptides; (i) moving, via the controller, the alkylated polypeptides, the elution buffer solution, the reducing reagent, and the alkylating reagent from the reaction chamber to the first holding coil via the third port; (j) moving, via the controller, the multi-port valve to a fourth position in which the first holding coil is connected to the desalting column via the fourth port of the multi-port valve, and, when the multi-port valve is in the fourth position, moving the alkylated polypeptides, the elution buffer solution, the reducing reagent, and the alkylating reagent from the first holding coil to the desalting column, whereby the denatured, reduced, and alkylated polypeptides are applied to the desalting column, thus separating the denatured, reduced, and alkylated polypeptides from the reducing and alkylating reagents, resulting in desalted polypeptides; (k) moving, via the controller, the desalted polypeptides to the proteolytic enzyme column, whereby the desalted polypeptides are digested; and (1) passing, via the controller, the digested polypeptides to an analytical device, whereby the digested polypeptides are analyzed.

Another aspect of the present disclosure provides a closed system for performing an online, real-time assay. The system includes: a first holding coil fluidly arranged to receive a sample of a product containing polypeptides; a multi-port valve fluidly coupled to and located downstream of the first holding coil; a polypeptide binding column fluidly coupled to the multi-port valve and arranged to receive the sample from the first holding coil via a first port of the multi-port valve, the polypeptide binding column configured to bind the polypeptides from the sample; a buffer source fluidly coupled to the multi-port valve and arranged to supply elution buffer solution to a second holding coil located downstream of the polypeptide binding column, such that the elution buffer solution is adapted to elute substantially all of the polypeptides from the polypeptide binding column; a reaction chamber fluidly coupled to the multi-port valve and arranged downstream of the polypeptide binding column, the reaction chamber adapted to receive a mixture from the polypeptide binding column via a second port of the multi-port valve, the mixture comprising the elution buffer solution and the eluted polypeptides, wherein the polypeptides of the mixture are denatured in the reaction chamber, wherein the reaction chamber is arranged to receive a reducing reagent that cleaves disulfide bond cros slinks via the first holding coil and a third port of the multi-port valve, the reducing reagent reduces the denatured polypeptides, and wherein the reaction chamber is further arranged to receive an alkylating reagent that alkylates sulfhydryls via the first holding coil and the third port of the multi-port valve, wherein the alkylating reagent alkylates the denatured and reduced polypeptides in the reaction chamber; a desalting column fluidly coupled to the multi-port valve and arranged to receive the denatured, reduced, and alkylated polypeptides, the elution buffer solution, and the alkylating reagent from the reaction chamber, the desalting column configured to separate the denatured, reduced, and alkylated polypeptides from the elution buffer solution, the reducing reagent, and the alkylating reagent; and a proteolytic enzyme column fluidly coupled to and arranged downstream of the second polypeptide column to obtain the separated polypeptides from the desalting column, the proteolytic enzyme column configured to digest the desalted polypeptides.

Another aspect of the present disclosure provides a closed system for performing a real-time assay. The system includes: a multi-port valve; a first holding coil upstream of the multi-port valve; a polypeptide binding column fluidly coupled to and downstream of a first port of the multi-port valve; a second holding coil fluidly coupled to and downstream of the polypeptide binding column; a reaction chamber fluidly coupled to and downstream of second and third ports of the multi-port valve; a desalting column fluidly coupled to and downstream of a fourth port of the multi-port valve; a proteolytic enzyme column downstream of the desalting column; and a controller communicatively coupled to the multi-port valve. The controller includes a memory, a processor, and logic stored on the memory and executable by the processor to: (a) move a sample of a product containing polypeptides to the first holding coil; (b) position the multi-port valve in a first position in which the first holding coil is connected to the polypeptide binding column via the first port of the multi-port valve, such that the sample flows to the first column, whereby polypeptides in the sample bind to the polypeptide binding column; (c) when the multi-port valve is in the first position, move an elution buffer solution from a source of elution buffer solution to the second holding coil via the polypeptide binding column, such that the elution buffer solution elutes substantially all of the polypeptides bound to the polypeptide binding column; (d) move the multi-port valve to a second position in which the second holding coil is connected to the reaction chamber via the second port of the multi-port valve; (e) when the multi-port valve is in the second position, move an elution/polypeptide mixture comprising the elution buffer solution and the eluted polypeptides to the reaction chamber, whereby the polypeptides in the elution/polypeptide mixture are denatured; (f) move the multi-port valve to a third position in which the first holding coil is connected to the reaction chamber via the third port of the multi-port valve; (g) after (f), move a reducing reagent that cleaves disulfide bonds to the first holding coil, and move the reducing reagent from the first holding coil to the reaction chamber via the third port of the multi-port valve, thereby reducing the denatured polypeptides; (h) after (g), move an alkylating reagent that alkylates sulfhydryls to the first holding coil, and move the alkylating reagent from the first holding coil to the reaction chamber via the third port, thereby alkylating the denatured and reduced polypeptides; (i) move the denatured, reduced, and alkylated polypeptides, the elution buffer solution, the reducing reagent, and the alkylating reagent from the reaction chamber to the first holding coil via the third port; (j) move the multi-port valve to a fourth position in which the first holding coil is connected to the desalting column via the fourth port of the multi-port valve, and, when the multi-port valve is in the fourth position, move the denatured, reduced, and alkylated polypeptides, the elution buffer solution, the reducing reagent, and the alkylating reagent from the first holding coil to the desalting column, whereby the denatured, reduced, and alkylated polypeptides are desalted; (k) move the desalted polypeptides to the proteolytic enzyme column, whereby the desalted polypeptides are digested; and (1) pass the digested polypeptides to a glycan analysis device, whereby the digested polypeptides are separated and quantified.

DETAILED DESCRIPTION OF THE PREFERRED EMBODIMENTS

The present disclosure provides for real-time assays and methods that allows for the monitoring and control of CQAs in real-time, so that the desired final polypeptide therapeutic product can be produced. The disclosed assays and methods can facilitate MAM result turn-around time such that results are available within a few hours (e.g., two to three hours) instead of a typical, manually operated, off-line measurement result of seven to ten days. Thus, the disclosed assays and methods improve the turn-around time by approximately 54-fold to 120-fold. Such "on-the-fly" (real time) results enable, for example, adjusting production variables to manufacture efficiently (online) products having appropriate CQAs.

Figure 1:
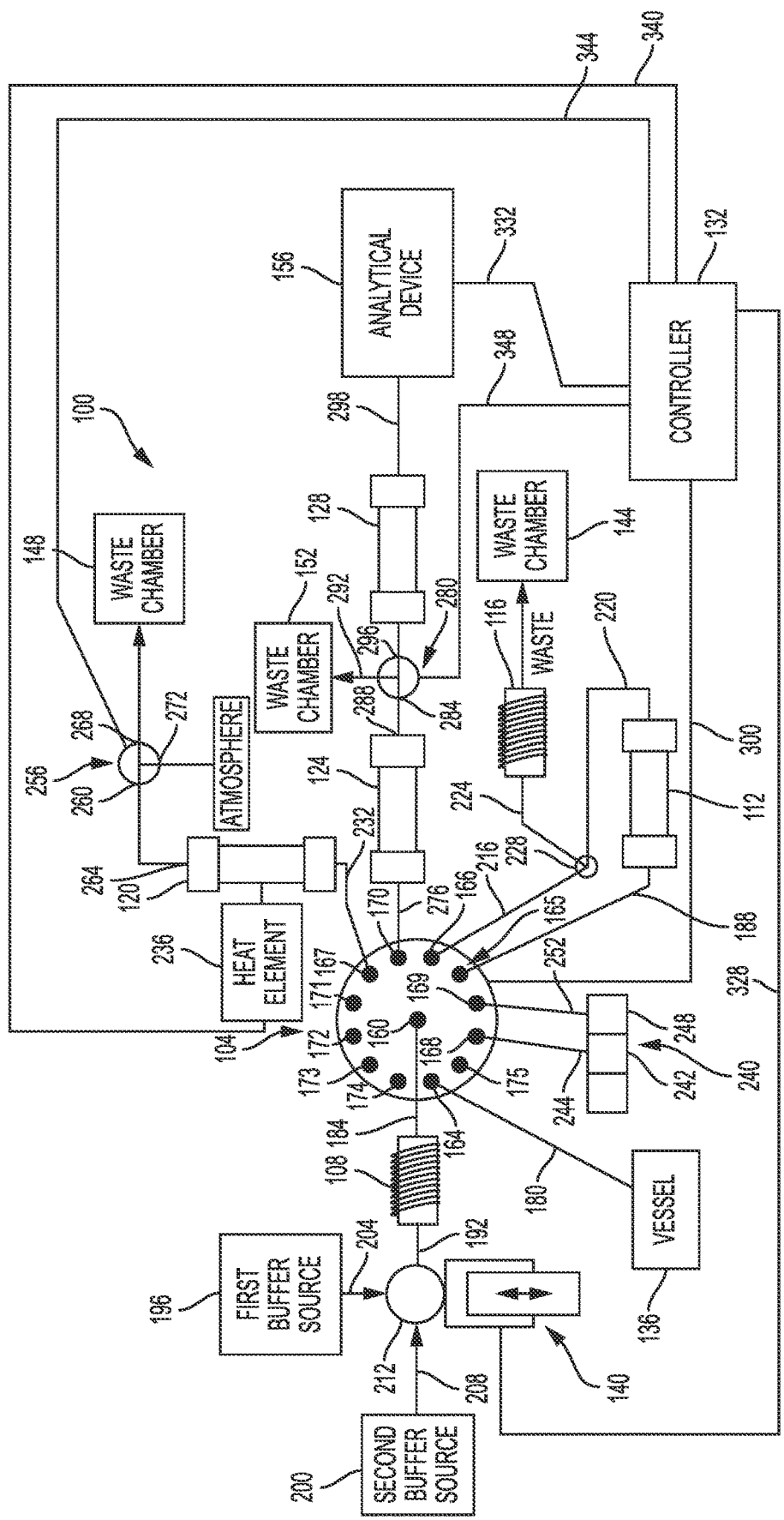
FIG. 1 is a schematic diagram of a system for performing an online, real-time assay assembled in accordance with the teachings of the present disclosure.

FIG. 1 illustrates a schematic diagram of a system 100 assembled in accordance with the teachings of the present disclosure. The system 100, which can be located at or in a laboratory (e.g., a Large Molecule Release Testing laboratory) is a closed system for automatically or substantially automatically performing an assay of a sample of a product containing polypeptides, as is described in greater detail below. By automating (or substantially automating) this process using the system 100, the assay can be performed in real-time (or substantially in real-time), such that the entire process can be performed, and the desired result obtained, in a matter of hours (e.g., 2 to 3 hours), a significant improvement over the 7 to 10 days typically required by the conventionally known, manually-operated MAM assays. Moreover, the closed nature of the process that utilizes the system 100 maintains sterile conditions.

In this version, the polypeptides can be therapeutic polypeptides, which are discussed further below.

The system 100 illustrated in FIG. 1 generally includes a multi-port valve 104, a first holding coil 108, a first column 112, a second holding coil 116, a reaction chamber 120, a second column 124, a third column 128, and a controller 132. In the version illustrated in FIG. 1, the system 100 also includes a vessel 136, a pump 140, a first waste chamber 144, a second waste chamber 148, a third waste chamber 152, and an analytical device 156 for analyzing the polypeptides. In other versions, however, the system 100 can not include one or more of these components. As an example, the system 100 can not include the vessel 136 and/or the analytical device 156. In any event, generally conventional plumbing extends between each of the components of the system 100 so as to facilitate fluid communication between components of the system 100 when desired, as is described in greater detail below. The multi-port valve 104 is generally configured to control fluid communication between the various components of the system 100. In this version, the multi-port valve 104 is a twelve satellite port and a central shared port valve. In other words, the multi-port valve 104 has a central port 160 and twelve satellite ports 164-175 that are selectively fluidly coupled to the central port 160. The multi-port valve 104 is movable between twelve different positions that fluidly couple the central port 160 with the twelve different satellite ports 164-175, respectively (some of which are not utilized in the operation of the system 100 of FIG. 1). In other versions, the multi-port valve 104 can include more or less satellite ports, can be a different type of valve or can be replaced by one or more different valves (each having one or more ports). As an example, the multi-port valve 104 can be replaced by a plurality of single port valves separately connected to and controlled by the controller 132, with each of the single port valves effectively replacing one of the satellite ports 164-175.

The vessel 136 is generally configured to hold or store the product containing polypeptides that is to be assayed. The vessel 136 in this version takes the form of a bioreactor that holds or stores the product. In other versions, however, the vessel 136 can instead take the form of a cell culture vessel, such as a flask, a plate, etc. The vessel 136 is fluidly coupled to the satellite port 164 of the valve 104 via a conduit 180 of the plumbing, such that the valve 104 can, when desired, obtain a sample of the product contained in the vessel 136 from the vessel 136.

The first holding coil 108 is located upstream of the valve 104 and is fluidly coupled to the central port 160 of the valve 104 via a conduit 184 of the plumbing. The first holding coil 108 is thus arranged to receive the sample of the product from the vessel 136, via the valve 104, when the valve 104 is in a first position in which the central port 160 is fluidly coupled to the satellite port 164.

The first column 112 is located downstream of the valve 104 and is fluidly coupled to the satellite port 165 of the valve 104 via a conduit 188 of the plumbing. The first column 112 is thus arranged to receive the sample from the first holding coil 108, via the valve 104, when the valve 104 is in a second position in which the central port 160 is fluidly coupled to the satellite port 165. When the first column 112 receives the sample, the first column 112 is configured to bind polypeptides from the sample as the sample flows therethrough. In this manner, the first column 112 separates the polypeptides in the sample from a remainder of the sample, which can be passed to the first waste chamber 144 via the second holding coil 116.

The first column 112, which can also be referred to herein as a polypeptide-binding column, is selected from the group consisting of a protein A column, a protein G column, a protein A/G column, a protein L column, an amino acid column, an avidin column, a streptavidin column, a carbohydrate bonding column, a carbohydrate column, a glutathione column, a heparin column, a hydrophobic interaction column, an immunoaffinity column, a nucleotide/coenzyme column, a specialty column, and an immobilized-metal affinity chromatography (IMAC) column. For example, in the case of polypeptides that are human IgGs of subclasses 1, 2, or 4, IgM, IgA, or IgE (and comprising a human Fc portion and/or a Fab region of the human VH3 family), protein A columns are useful. Protein G columns can be used to purify human IgGs of subclasses 1-4. Recombinant fusion protein A/G columns can also be used to purify all of these classes of human antibodies, as the fusion protein provides protein A and protein G binding sites. Thus, protein A/G fusion proteins can be used to purify human IgG, IgA, IgE, and IgM. Furthermore, protein L columns can be used to purify human IgG, IgM, IgA, IgE and IgD, provided the target antibodies have an appropriate kappa (κ) subtype light chain (i.e., VκI, VκIII and VκIV subtypes); protein L columns can also be used to purify Fab and scFv fragments also having the appropriate K chain subtype, as protein L binds the variable (V) chain of antibodies.

The pump 140 is located upstream of and fluidly coupled to the first holding coil 108 via a conduit 192 of the plumbing. The pump 140 in this version takes the form of a syringe pump that is fluidly coupled to both a first buffer source 196 and a second buffer source 200. In this version, the first buffer source 196 is a elution buffer source that can supply an elution buffer solution 204, e.g., in the case of protein A-bound antibodies, an acidic buffer; or in the case of protein G-bound antibodies, very acidic (pH 3 or less) buffer; one of skill in the art is able to optimize and select appropriate elution buffers for bound antibodies, to the pump 140 (and, ultimately, the first holding coil 108), and the second buffer source 200 is a denaturing buffer (containing a denaturant that disrupts quaternary, tertiary, or secondary polypeptide structure) source that can supply a denaturing reagent 208 to the pump 140 (and, ultimately, the first holding coil 108). In other versions, the pump 140 can be a different type of pump and/or different pumps 140 can be used for each of the buffer sources 196, 200.

In some versions, the denaturing reagent can be or include a denaturing detergent or a chaotrope. In those versions in which the denaturing reagent is or includes a denaturing detergent, the denaturing detergent is preferably selected from the group consisting of sodium dodecyl sulfate (SDS), sodium cholate, sodium deoxycholate, sodium glycocholate, sodium taurocholate, sodium taurodeoxycholate, N-lauroylsarcosine, lithium dodecyl sulfate, hexadecyltrimethyl ammonium bromide (CTAB) and trimethyl(tetradecyl) ammonium bromide (TTAB). More preferably, the denaturing detergent is SDS. In those versions in which the denaturing reagent is or includes a chaotrope, the chaotrope is preferably selected from the group consisting of urea, n-butanol, ethanol, guanidinium chloride, lithium perchlorate, lithium acetate, magnesium chloride, phenol, 2-propanol, and thiourea. Alternatively or additionally, the denaturing reagent can be or include a heated fluid that has a temperature suitable for reaching, if not maintaining, a pre-determined temperature (e.g., about 22° C. to about 120° C.) in the reaction chamber 120 when the denaturing reagent is passed to the reaction chamber 120.

A valve 212 is located between the pump 140 and the first and second buffer sources 196, 200 to selectively fluidly couple the pump 140 to only one of the buffer sources 196, 200 at a time. More particularly, the valve 212 is movable between a first position, in which the pump 140 is fluidly coupled to the first buffer source 196 and the pump 140 is fluidly isolated from the second buffer source 200, and a second position, in which the pump 140 is fluidly coupled to the second buffer source 200 and the pump 140 is fluidly isolated from the first buffer source 196. In other words, the pump 140 is selectively fluidly coupled to the first buffer source 196 or the second buffer source 200 depending upon the position of the valve 212.

As noted above, the pump 140 in this version is a syringe pump. The syringe pump 140 is generally configured to obtain a buffer from one of the buffer sources 196, 200 and output that buffer to the first holding coil 108. When the valve 212 is in the first position, the pump 140 can obtain (e.g., draw in) the elution buffer solution 204 from the first buffer source 196, and, when desired, can output (e.g., eject) that elution buffer solution 204 to the first holding coil 108. Conversely, when the valve 212 is in the second position, the pump 140 can obtain (e.g., draw in) the denaturing reagent 208 from the second buffer source 200, and, when desired, can output (e.g., eject) that denaturing reagent 208 to the first holding coil 108.

The second holding coil 116 is located downstream of the valve 104, the first holding coil 108, and the first column 112. The second holding coil 116 is selectively fluidly coupled to the satellite port 166 of the valve 104 via conduits 216, 220 of the plumbing. The second holding coil 116 is also selectively fluidly coupled to the first column 112 via the conduit 220 and a conduit 224. A three-way valve 228 is arranged between the conduits 216, 220, 224 to facilitate the selective coupling in order to produce the desired fluid flow, as is described in greater detail below.

The second holding coil 116 is thus arranged to receive the elution buffer solution 204 from the first holding coil 108, via the valve 104 and through the first column 112, when the pump 140 outputs the elution buffer solution 204 in the manner described above, the valve 104 is in the second position in which the central port 160 is fluidly coupled to the satellite port 165. As the elution buffer solution 204 passes through the first column 112, the elution buffer solution 204 elutes substantially all of the polypeptides bound to the first column 112. The three-way valve 228 is operated to connect the conduits 220, 224, thereby fluidly coupling the first column 112 with the second holding coil 116, such that an elution/polypeptide mixture including the elution buffer solution 204 and the eluted polypeptides flows from the first column 112 to the second holding coil 116 via the conduits 220, 224.

The reaction chamber 120 is located downstream of the valve 104 and the first column 112, and is fluidly coupled to the satellite port 167 of the valve 104 via conduit 232 of the plumbing. In this version, the reaction chamber 120 is partially, if not completely, pre-filled with the denaturing reagent 208 (i.e., filled prior to operation of the system 100) from the second buffer source 200 by using the pump 140 to output the denaturing reagent 208 to the first holding coil 108 and moving the multi-port valve 104 to a fourth position in which the central port 160 is fluidly coupled to the satellite port 167 of the valve 167, thereby facilitating movement of the denaturing reagent 208 from the first holding coil 108 to the reaction chamber 120. In other versions, however, the reaction chamber 120 can be partially or completely filled with the denaturing reagent 208 during operation of the system 100 (e.g., after the second holding coil 116 receives the elution buffer solution 204), partially or completely filled with a denaturing reagent from another buffer source and/or in a different manner, or the reaction chamber 120 may not be filled at all, in which case heat can be applied to the reaction chamber 120 by a heating element 236 connected to the reaction chamber 120.

After the elution/polypeptide mixture reaches the second holding coil 116, the elution/polypeptide mixture is moved to the reaction chamber 120. In this version, the reaction chamber 120 indirectly receives the elution/polypeptide mixture from the second holding coil 116. More particularly, the three-way valve 228 is operated to connect the conduits 216, 224, the elution/polypeptide mixture is moved from the second holding coil 116 to the satellite port 166 of the multi-port valve 104 via the conduits 216, 224, the valve 104 is moved to a third position in which the central port 160 is fluidly coupled to the satellite port 166, such that the mixture moves to the first holding coil 108, and the valve 104 is moved to a fourth position in which the central port 160 is fluidly coupled to the satellite port 167 of the valve 104, such that the mixture moves from the first holding coil 108 to the reaction chamber 120. In other versions, the reaction chamber 120 can directly receive the elution/polypeptide mixture from the second holding coil 116 or can indirectly receive the mixture from the second holding coil 116 utilizing one or more different components and/or in a different order.

In any case, once the elution/polypeptide mixture reaches the reaction chamber 120, the polypeptides in the mixture incubate in the reaction chamber 120, thereby denaturing the polypeptides in the reaction chamber 120. When, for example, the reaction chamber 120 is at least partially filled with the denaturing reagent, the polypeptides in the mixture will, upon reaching the reaction chamber 120 and reacting with the denaturing reagent, undergo denaturation. In some cases, the reaction chamber 120 can, at the same time or at all times, be heated by the heating element 236 connected to (e.g., positioned immediately adjacent, surrounding) the reaction chamber 120 to help facilitate the denaturation process. In other words, the heating element 236 can apply heat, preferably heat having a temperature of about 22° C. to about 120° C. and, more preferably, heat having a temperature of about 40° C., to the reaction chamber 120 to encourage denaturation. The heating element 236 can, for example, take the form of a heating block, a heating coil, an induction heater, a heat pump, a cartridge heater, an electrical resistance wire, a heated fluid, or other element suitable for heating one or more portions of the reaction chamber 120. In any event, by applying heat from the heating element 236 to the reaction chamber 120, the process of denaturation can be facilitated. In other cases, however, the reaction chamber 120 can not be filled with the denaturing reagent and the denaturation process can be facilitated only by applying heat from the heating element 236.

Following the denaturation of the polypeptides in the mixture, the reaction chamber 120 is configured to receive a reducing reagent that cleaves disulfide bond crosslinks, thereby reducing the denatured polypeptides. The reducing reagent can be selected from the group consisting of dithiothreitol (DTT), glutathione, β-mercaptoethanol (β-ME), and tris(2-carboxyethyl)phosphine (TCEP) and is generally supplied by cooling vessel 240, which can, for example, take the form of a chiller having a temperature of 4° C. In this version, the cooling vessel 240 is located downstream of the valve 104 and has a first chamber 242 that contains the reducing reagent and is fluidly coupled to the satellite port 168 of the valve 104 via a conduit 244 of the plumbing. The first chamber 242 supplies the reducing reagent to the first holding coil 108 when the valve 104 is in a fifth position in which the central port 160 is fluidly coupled to the satellite port 168 of the valve 104, and the reducing reagent is then moved from the first holding coil 108 to the reaction chamber 120 when the valve 104 is in (or returns to) the fourth position (in which the central port 160 is fluidly coupled to the satellite port 167). Thus, in this version, the reducing reagent is indirectly supplied to the reaction chamber 120 via the first holding coil 108. In other versions, however, the first chamber 242 can directly supply the reducing reagent to the reaction chamber 120 (i.e., without moving the reducing reagent to the first holding coil 108).

After the denatured polypeptides are reduced, the reaction chamber 120 is configured to receive an alkylating agent that alkylates sulfhydryls in the reaction chamber 120, thereby alkylating the denatured and reduced polypeptides in the reaction chamber 120. The alkylating agent is preferably an alkylating reagent such as indole-3-acetic acid (IAA), though other alkylating agents can be used. In this version, the cooling vessel 240 has a second chamber 248 that contains the alkylating agent and is fluidly coupled to the satellite port 169 of the valve 104 via conduit 252 of the plumbing. The second chamber 248 supplies the alkylating agent to the first holding coil 108 when the valve 104 is in a sixth position in which the central port 160 is fluidly coupled to the satellite port 169 of the valve 104, and the alkylating agent is then moved from the first holding coil 108 to the reaction chamber 120 when the valve 104 is in (or returns) to the fourth position. Thus, in this version, the alkylating agent is indirectly supplied to the reaction chamber 120 via the first holding coil 108. In other versions, however, the second chamber 248 can directly supply the alkylating agent to the reaction chamber 120 (i.e., without moving the alkylating agent to the first holding coil 108) and/or the alkylating agent can be supplied from a different cooling vessel (e.g., a cooling vessel separate from the cooling vessel 240).

In this version, the system 100 further includes a first normally open valve 256 that is fluidly coupled to and located downstream of the reaction chamber 120. The normally open valve 256 has an inlet port 260 that is fluidly connected to an outlet 264 of the reaction chamber 120, a first outlet port 268 that is fluidly connected to the second waste chamber 148, and a second outlet port 272 that is fluidly connected to atmosphere. The normally open valve 256 normally operates in an open, or first, position when the system 100 is in operation and, more particularly, the reaction chamber 120 is receiving and being filled with the elution/polypeptide mixture, the reducing reagent, the alkylating agent, and, in some cases, the denaturing reagent, the valve 256. In this open position, the inlet port 260 is fluidly coupled to the first outlet port 268 and the inlet port 260 is fluidly isolated from the second outlet port 272, such that when the reaction chamber 120 is filled beyond its fixed volume, any excess contents are directed to the second waste chamber 148. However, the normally open valve 256 is movable (e.g., by applying a current to the valve 256) from the open position to a closed, or second, position when, for example, the reaction chamber 120 is no longer receiving the above-described contents and it is time to clean the reaction chamber 120. In this closed position, the inlet port 260 is fluidly coupled to the second outlet port 272 and the inlet port 260 is fluidly isolated from the first outlet port 268, such that the outlet 264 of the reaction chamber 120 is exposed to the atmosphere. In turn, air can flow into the reaction chamber 120, thereby facilitating the removal of contents from the reaction chamber 120.

The second column 124, also referred to herein as the desalting column 124, preferably takes the form of a size exclusion chromatography column that is located downstream of the valve 104 and is fluidly coupled to the satellite port 170 of the valve 104 via a conduit 276 of the plumbing. The second column 124 is thus arranged to receive the denatured, reduced, and alkylated polypeptides, the elution buffer solution 204, the alkylating agent, the reducing reagent, and the denaturing reagent (when one is used) from the reaction chamber 120. In this version, the second column 124 indirectly receives these materials from the reaction chamber 120. More particularly, these materials are moved from the reaction chamber 120 to the first holding coil 108, via the valve 104, when the valve 104 is in (or moved to) the fourth position (in which the central port 160 is fluidly coupled to the satellite port 167), and the valve 104 is moved to a seventh position in which the central port 160 is fluidly coupled to the satellite port 170, such that the materials move from the first holding coil 108 to the second column 124. In other versions, the second column 124 can directly receive these materials from the reaction chamber 120 or can indirectly receive these materials utilizing one or more different components and/or in a different order.

In any event, when the second column 124 receives the denatured, reduced, and alkylated polypeptides, the elution buffer solution 204, the alkylating agent, the reducing reagent, and the denaturing reagent (when one is used), the second column 124 is configured to separate the denatured, reduced, and alkylated polypeptides from the elution buffer solution 204, the alkylating agent, the reducing reagent, and the denaturing reagent (when used), which are ultimately moved to the third waste chamber 152. Thus, the second column 124 can be referred to herein as the desalting column 124. At the same time, the second column 124 is configured to buffer exchange the polypeptides into a desired buffer condition that allow the third column 128 to perform the functionality described below.

In this version, the system 100 further includes a second normally open valve 280 that is fluidly coupled to and located between the second column 124 and the third column 128. The normally open valve 280 has an inlet port 284 that is fluidly connected to an outlet 288 of the second column 124, a first outlet port 292 that is fluidly connected to the third waste chamber 152, and a second outlet port 296 that is fluidly connected to the third column 128. The normally open valve 280 normally operates in an open, or first, position when the system 100 is in operation. In this open position, the inlet port 284 is fluidly coupled to the first outlet port 292 and the inlet port 284 is fluidly isolated from the second outlet port 296, such that the elution buffer solution 204, the alkylating agent, the reducing reagent, and the denaturing reagent are directed to the third waste chamber 152. However, the normally open valve 280 is movable (e.g., by applying a current to the valve 280) from the open position to a closed, or second, position when it is desired to move the desalted polypeptides from the second column 124 to the third column 128, which is located downstream of the second column 124. In this closed position, the inlet port 284 is fluidly coupled to the second outlet port 296 and the inlet port 284 is fluidly isolated from the first outlet port 292, such that the second column 124 is fluidly coupled to the third column 128, such that the desalted can pass from the second column 124 to the third column 128. In this version, the third column 128 includes a proteolytic enzyme (e.g., an endopeptidase selected from the group consisting of trypsin, chymotrypsin, elastase, thermolysin, pepsin, glutamyl endopeptidase, neprilysin, Lys-C protease, and *Staphylococcus aureus* V8 protease), such that the third column 128 can be referred to herein as a proteolytic enzyme column. In any case, the third column 128 digests the desalted polypeptides obtained from the second column 124.

After the polypeptides have been digested in the third column 128, the digested polypeptides can be moved to the analytical device 156, which can, for example, take the form of a liquid chromatography device, a high-performance liquid chromatography device, an ultra high-performance liquid chromatography device, a mass spectrometry device, a glycan analysis device, another analysis device, or a combination thereof. In this version, the analytical device 156 is located downstream of the third column 128 and is fluidly coupled to the third column 128 via a conduit 298 of the plumbing. Thus, in this version, the digested polypeptides can be automatically moved to the analytical device 156 for analysis (e.g., for quantification and separation). In other versions, however, the analytical device 156 is not be part of the system 100 (e.g., not fluidly coupled to the third column 128), in which case the digested polypeptides can be moved to the analytical device 156 in a different manner (e.g., manually).

As briefly noted above, the system 100 also includes the controller 132, which in this version is communicatively coupled or connected to various components of the system 100 to monitor and facilitate or direct the above-described operation of the system 100 by transmitting signals (e.g., control signals, data) to and receiving signals (e.g., data) from the various components of the system 100. The controller 132 can be located immediately adjacent the other components of the system 100 (e.g., in the same environment as the system 100) or can be remotely located from the other components of the system 100. As illustrated, the controller 132 is communicatively coupled or connected to the multi-port valve 104 via a communication network 300, the pump 140 via a communication network 328, the analytical device 156 via a communication network 332, the heating element 236 via a communication network 340, the first normally open valve 256 via a communication network 344, and the second normally open valve 280 via a communication network 348. In other versions, the controller 132 can be communicatively coupled or connected to more or less components of the system 100, e.g., the first holding coil 108, the first column 112, the second holding coil 116, the reaction chamber 120, the second column 124, the third column 128, the vessel 136, the three-way valve 228, and/or the cooling vessel 240.

As used herein, the phrases "communicatively coupled" and "connected" are defined to mean directly coupled or connected to or indirectly coupled or connected through one or more intermediate components. Such intermediate components can include hardware and/or software-based components. It is appreciated that the networks 300-348 can be wireless networks, wired networks, or combinations of a wired and a wireless network (e.g., a cellular telephone network and/or 802.11x compliant network), and can include a publicly accessible network, such as the Internet, a private network, or a combination thereof. The type and configuration of the networks 300-348 is implementation dependent, and any type of communications networks which facilitate the described communications between the controller 132 and the components of the system 100, available now or later developed, can be used.

Figure 2:
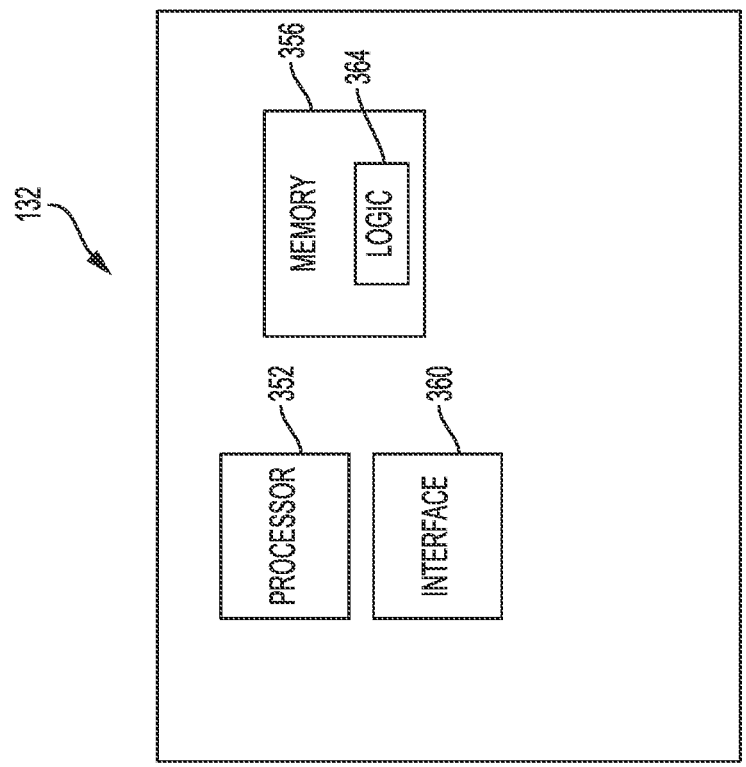
FIG. 2 is a schematic diagram of a controller of the system illustrated in FIG. 1.

As shown in FIG. 2, the controller 132 includes a processor 352, a memory 356, a communications interface 360, and computing logic 364. The processor 352 can be a general processor, a digital signal processor, an application-specific integrated circuit (ASIC), field programmable gate array, graphics processing unit, analog circuit, digital circuit, or any other known or later developed processor. The processor 352 operates pursuant to instructions in the memory 356. The memory 356 can be a volatile memory or a non-volatile memory. The memory 356 can include one or more of a read-only memory (ROM), random-access memory (RAM), a flash memory, an electronic erasable program read-only memory (EEPROM), or other type of memory. The memory 356 can include an optical, magnetic (hard drive), or any other form of data storage device.

The communications interface 360 is provided to enable or facilitate electronic communication between the controller 132 and the components of the refrigeration system 100 via the networks 300-348. The communications interface 360 can be or include, for example, one or more universal serial bus (USB) ports, one or more Ethernet ports, and/or one or more other ports or interfaces. The electronic communication can occur via any known communications protocol, including, by way of example, USB, RS-232, RS-485, WiFi, Bluetooth, and/or any other suitable communications protocol.

The logic 364 generally includes one or more control routines and/or one or more sub-routines embodied as computer-readable instructions stored on the memory 356. The control routines and/or sub-routines can perform PID (proportional-integral-derivative), fuzzy logic, nonlinear, or any other suitable type of control. The processor 352 generally executes the logic 364 to perform actions related to the operation of the system 100.

Generally speaking, the logic 364, when executed, causes the processor 352 to control components of the system 100, particularly the multi-port valve 104, the pump 140, the heat element 236, the first and second normally open valves 256, 280, and the analytical device 156, such that the system 100 operates in the desired manner discussed herein. More particularly, the logic 364 can, when executed, cause the processor 352 to (i) move the multi-port valve 104 to or between any of the positions described herein, thereby fluidly coupling various components of the system 100 as described above, (ii) control the pump 140 (e.g., cause the pump 140 to obtain and output the elution buffer solution 204 or the denaturing reagent 208), (iii) control the heating element 236 (when employed in the system 100) to selectively apply heat to the reaction chamber 120 (and the contents thereof), (iv) control the first normally open valve 256, (v) control the second normally open valve 280, (vi) control the analytical device 156, and perform other desired functionality.

When, for example, it is desired to perform a real-time assay of a sample of a product containing polypeptides, the logic 364 is executable by the processor 352 to position the valve 104 in the first position described above, move the sample of the product from the vessel 136 to the first holding coil 108 via the conduit 180, the port 164, the port 160, position the valve 104 in the second position described above, and move the sample from the first holding coil 108 to and through the polypeptide-binding column 112 via the conduit 184, the ports 160, 164, and the conduit 188. In turn, substantially all of the polypeptides in the sample bind to the column 112, such that the polypeptides in the sample are separated from the remainder of the sample, which passes to the first waste chamber 144 via the conduits 220, 224 and the second holding coil 116.

The logic 364 is further executable by the processor 352 to cause the pump 140 to obtain the elution buffer solution 204 from the first buffer source 196 and output the elution buffer solution 204 to the first holding coil 108 via the conduit 192. In some cases, the pump 140 can need to be moved from the second position to the first position (to fluidly couple the pump 140 with the first buffer source 196), but in other cases, the pump 140 can already be in the first position. In any case, the logic 364 is executable by the processor 352 to move the elution buffer solution 204 from the first holding coil 108 to and through the first column 112 and to the second holding coil 116, via the conduit 184, the ports 160, 165, and the conduits 188, 220, and 224. In this manner, the elution buffer solution 204 elutes substantially all of the polypeptides bound to the first column 112, and an elution/polypeptide mixture including the elution buffer solution 204 and the eluted polypeptides flows from the first column 112 to the second holding coil 116.

The logic 364 is further executable by the processor 352 to move the valve 104 to the third position described above, move the elution/polypeptide mixture from the second holding coil 116 to the first holding coil 108, via the conduits 224, 216, the ports 166, 160, and the conduit 184, move the valve 104 to the fourth position described above, and move the elution/polypeptide mixture from the first holding coil 108 to the reaction chamber 120, via the conduit 184, the ports 160, 167, and the conduit 232. In turn, the polypeptides in the elution/polypeptide mixture are incubated in the reaction chamber 120 with the denaturing reagent 208 and/or in the presence of heat applied by the heating element 236, which thereby denatures the polypeptides.

The logic 364 is further executable by the processor 352 to move the valve 104 to the fifth position described above, move the reducing reagent from the first chamber 242 of the cooling vessel 240 to the first holding coil 108 via the conduit 244, the ports 168, 160, and the conduit 184, move the valve 104 back to the fourth position, and move the reducing reagent from the first holding coil 108 to the reaction chamber 120, via the conduit 184, the ports 160, 167, and the conduit 232. Upon reaching the reaction chamber 120, the reducing reagent cleaves disulfide bond crosslinks, which thereby reduces the denatured polypeptides in the reaction chamber 120.

The logic 364 is further executable by the processor 352 to move the valve 104 to the sixth position described above, move the alkylating agent from the second chamber 248 of the cooling vessel 240 to the first holding coil 108 via the conduit 252, the ports 169, 160, and the conduit 184, move the valve 104 back to the fourth position, and move the alkylating agent from the first holding coil 108 to the reaction chamber 120, via the conduit 184, the ports 160, 167, and the conduit 232. Upon reaching the reaction chamber 120, the alkylating agent alkylates sulfhydryls in the reaction chamber 120, which thereby alkylates the denatured and reduced polypeptides in the reaction chamber 120.

The logic 364 is further executable by the processor 352 to move the valve 104 to the fourth position (if not already there), move the denatured, reduced, and alkylated polypeptides, the elution buffer solution 204, the alkylating agent, the reducing reagent, and the denaturing reagent (when used) from the reaction chamber 120 to the first holding coil 108, via the conduit 232, the ports 167, 160, and the conduit 184, move the valve 104 to the seventh position described above, and move the denatured, reduced, and alkylated polypeptides, the elution buffer solution 204, the alkylating agent, the reducing reagent, and the denaturing reagent (when used) from the first holding coil 108 to the desalting column 124 via the conduit 184, the ports 160, 170, and the conduit 276. In turn, the desalting column 124 separates the denatured, reduced, and alkylated polypeptides from the elution buffer solution 204, the alkylating agent, the reducing reagent, and the denaturing reagent, which are passed or move to the third waste chamber 152.

At some point after the denatured, reduced, and alkylated polypeptides, the elution buffer solution 204, the alkylating agent, the reducing reagent, and the denaturing reagent (when used) are moved from the reaction chamber 120 to the first holding coil 108, the logic 364 is further executable by the processor 352 to move the normally open valve 256 from its open, first position, wherein the outlet 264 of the chamber 120 is fluidly coupled to the second waste chamber 148 so as to direct contents that will not fit in the reaction chamber 120 (as a result of it being filled beyond its fixed volume) to the second waste chamber 148, to its closed, second position, wherein the outlet 264 is fluidly coupled to atmosphere, such that air can flow into the reaction chamber 120, thereby facilitating the removal of contents from the reaction chamber 120. The normally open valve 256 can return to the open, first position immediately after the reaction chamber 120 has been emptied or can return to the open, first position at a later point in time.

After the desalting column 124 separates the denatured, reduced, and alkylated polypeptides from the other materials, the logic 364 is further executable by the processor 352 to move the normally open valve 280 from its open, first position, wherein the inlet port of the valve 280 is fluidly coupled to the third waste chamber 152, to its closed, second position, wherein the inlet port of the valve 280 is fluidly coupled to the proteolytic enzyme column 128. In turn, the logic 364 is executable by the processor 352 to move the desalted (or separated) polypeptides from the desalting column 124 to the proteolytic enzyme column 128, which digests the desalted polypeptides.

After the polypeptides have been digested, the logic 364 is, at least in this version, further executable by the processor 352 to move the digested polypeptides from the proteolytic enzyme column 128 to the analytical device 156 for analysis of the polypeptides, and to cause the analytical device 156 to perform the desired analysis. As an example, the logic 364 can, when executed by the processor 352, cause the analytical device 156 to separate and quantify the polypeptides.

In other versions, the logic 364 can, when executed by the processor 352, cause additional, less, and/or different functionality to be performed. As an example, the logic 364, when executed by the processor 352, may not move the digested polypeptides from the column 128 to the analytical device 156 or cause the analytical device 156 to perform the desired analysis. Moreover, in other versions, the logic 364 can be executed by the processor 352 in a different order than described herein. Finally, it is appreciated that the logic 364 can be executed by the processor 352 any number of different times, as the system 100 can be used to perform real-time analyses of multiple samples (from the same product and/or from a different product).

Figure 3A:
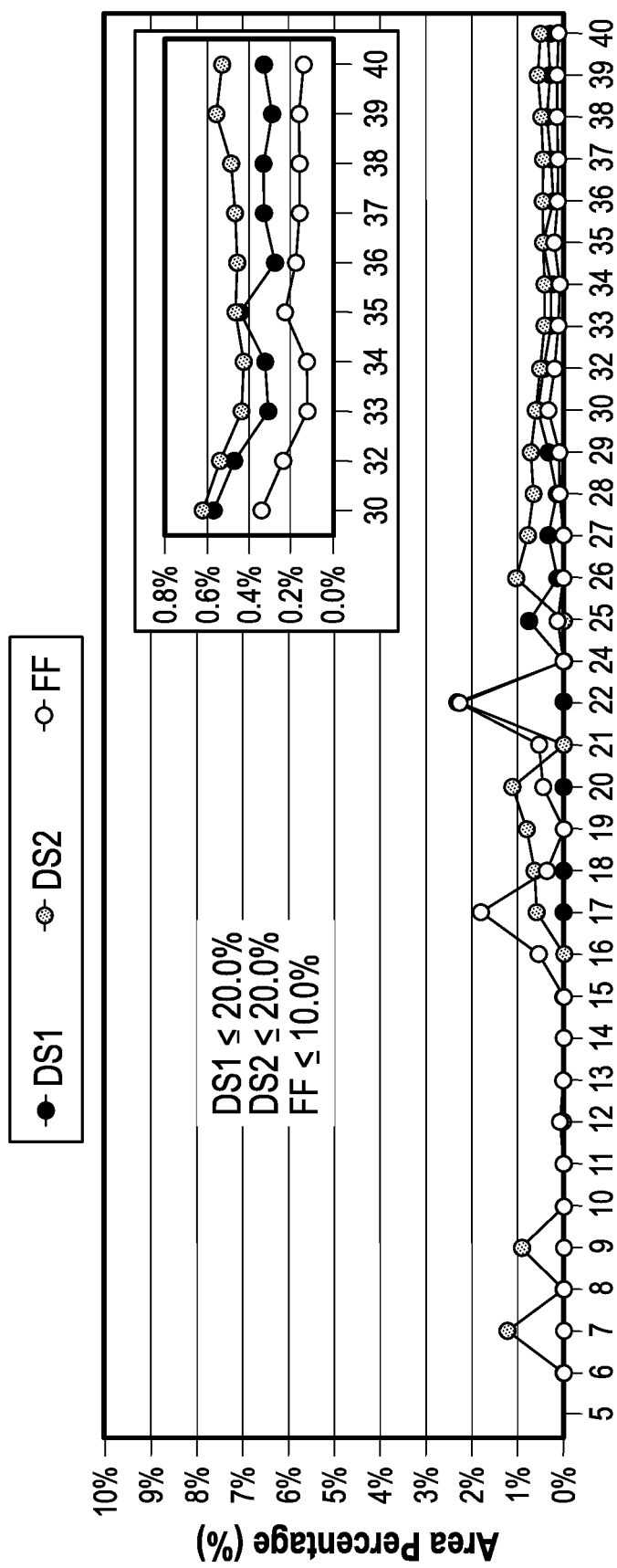
FIGS. 3A and 3B are graphs depicting the results of a study monitoring the effectiveness of the system of FIG. 1 over a production run of 40 days.
Figure 3B:
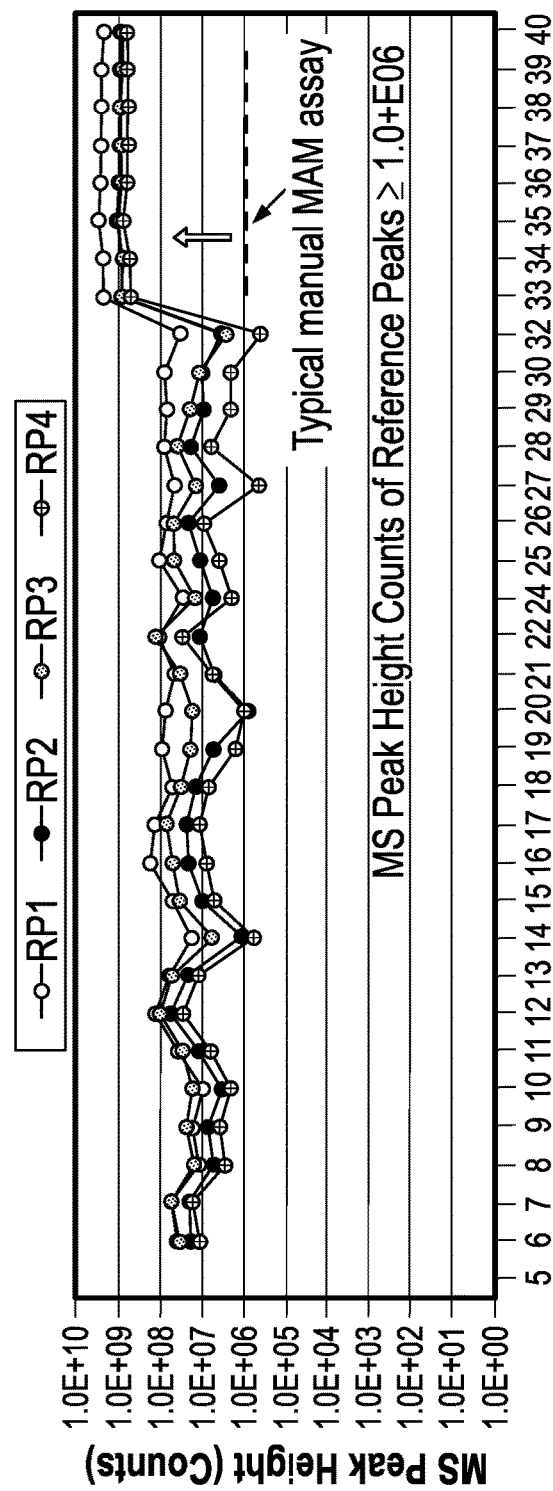
Figure 3C:
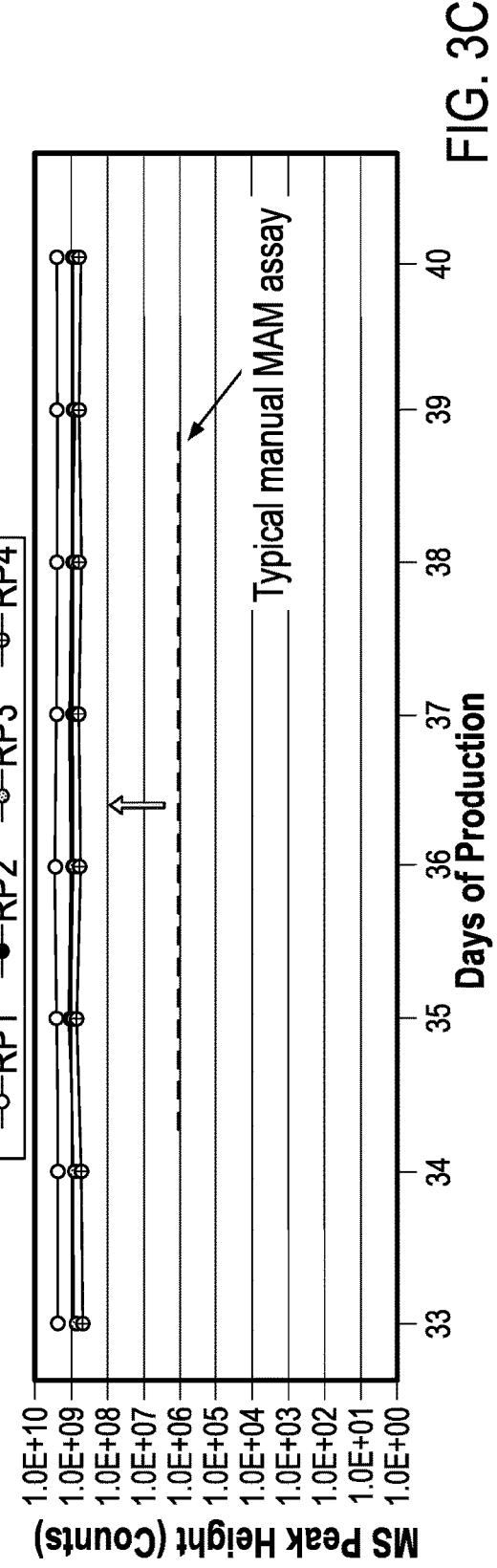
FIG. 3C is a graph depicting a snapshot of the results of FIG. 3B over a 8 day period of time.

FIGS. 3A-3C illustrate the results of an online and real-time MAM assay study designed to monitor the effectiveness of the system 100 in preparing a sample of a product containing a Bispecific T-cell Engager (BiTE®) molecule. In particular, the study monitored the effectiveness of the system 100 over a production run of 40 days. The study began monitoring and collecting CQA data, such as area percentage for 2 deamidation sites, DS1 and DS2, and the frequency of a fragmentation, FF, illustrated in FIG. 3A, and MS peak height (expressed as a number of ion counts) for four reference peptides RP1, RP2, RP3, and RP4, illustrated in FIGS. 3B and 3C, on day 6 of the 40-day production run. As illustrated in FIG. 3A, the system 100 capably and effectively performed the intended functionality discussed herein over the entire duration of the 40-day production run, and, as illustrated in FIGS. 3B and 3C, the CQA data collected between day 6 and day 40 was substantially consistent, i.e., there was no significant change in product quality over time, and the product quality actually increased after day 32, thereby demonstrating the robustness of the system 100 in automatically preparing the sample. Indeed, as illustrated in FIG. 3C, the CQA data collected for RP1, RP2, RP3, and RP4 during that time-period was better than the CQA data obtained during a typical manual MAM assay.

Therapeutic Polypeptides

Proteins, including those that bind to one or more of the following, can be useful in the disclosed devices and methods. These include CD proteins, including CD3, CD4, CD8, CD19, CD20, CD22, CD30, and CD34; including those that interfere with receptor binding. HER receptor family proteins, including HER2, HER3, HER4, and the EGF receptor. Cell adhesion molecules, for example, LFA-I, Mol, p150, 95, VLA-4, ICAM-I, VCAM, and alpha v/beta 3 integrin. Growth factors, such as vascular endothelial growth factor ("VEGF"), growth hormone, thyroid stimulating hormone, follicle stimulating hormone, luteinizing hormone, growth hormone releasing factor, parathyroid hormone, Mullerian-inhibiting substance, human macrophage inflammatory protein (MIP-I-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-α and TGF-β, including TGF-β1, TGF-β2, TGF-β3, TGF-β4, or TGF-β5, insulin-like growth factors-I and -II (IGF-I and IGF-II), des(1-3)-IGF-I (brain IGF-I), and osteoinductive factors. Insulins and insulin-related proteins, including insulin, insulin A-chain, insulin B-chain, proinsulin, and insulin-like growth factor binding proteins. Coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin; (vii) other blood and serum proteins, including but not limited to albumin, IgE, and blood group antigens. Colony stimulating factors and receptors thereof, including the following, among others, M-CSF, GM-CSF, and G-CSF, and receptors thereof, such as CSF-1 receptor (c-fms). Receptors and receptor-associated proteins, including, for example, flk2/flt3 receptor, obesity (OB) receptor, LDL receptor, growth hormone receptors, thrombopoietin receptors ("TPO-R," "c-mpl"), glucagon receptors, interleukin receptors, interferon receptors, T-cell receptors, stem cell factor receptors, such as c-Kit, and other receptors. Receptor ligands, including, for example, OX40L, the ligand for the OX40 receptor. Neurotrophic factors, including bone-derived neurotrophic factor (BDNF) and neurotrophin-3, -4, -5, or -6 (NT-3, NT-4, NT-5, or NT-6). Relaxin A-chain, relaxin B-chain, and prorelaxin; interferons and interferon receptors, including for example, interferon-α, -β, and -γ, and their receptors. Interleukins and interleukin receptors, including IL-I to IL-33 and IL-I to IL-33 receptors, such as the IL-8 receptor, among others.

Viral antigens, including an AIDS envelope viral antigen. Lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, DNAse, inhibin, and activin. Integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antibodies. Myostatins, TALL proteins, including TALL-I, amyloid proteins, including but not limited to amyloid-beta proteins, thymic stromal lymphopoietins ("TSLP"), RANK ligand ("OPGL"), c-kit, TNF receptors, including TNF Receptor Type 1, TRAIL-R2, angiopoietins, and biologically active fragments or analogs or variants of any of the foregoing.

Exemplary polypeptides and antibodies include Activase® (Alteplase); alirocumab, Aranesp® (Darbepoetin-alfa), Epogen® (Epoetin alfa, or erythropoietin); Avonex® (Interferon β-Ia); Bexxar® (Tositumomab); Betaseron® (Interferon-β); bococizumab (anti-PCSK9 monoclonal antibody designated as L1L3, see U.S. Pat. No. 8,080,243); Campath® (Alemtuzumab); Dynepo® (Epoetin delta); Velcade® (bortezomib); MLN0002 (anti-α4(37 mAb); MLN1202 (anti-CCR2 chemokine receptor mAb); Enbrel® (etanercept); Eprex® (Epoetin alfa); Erbitux® (Cetuximab); evolocumab; Genotropin® (Somatropin); Herceptin® (Trastuzumab); Humatrope® (somatropin [rDNA origin] for injection); Humira® (Adalimumab); Infergen® (Interferon Alfacon-1); Natrecor® (nesiritide); Kineret® (Anakinra), Leukine® (Sargamostim); LymphoCide® (Epratuzumab); Benlysta™ (Belimumab); Metalyse® (Tenecteplase); Mircera® (methoxy polyethylene glycol-epoetin beta); Mylotarg® (Gemtuzumab ozogamicin); Raptiva® (efalizumab); Cimzia® (certolizumab pegol); Soliris™ (Eculizumab); Pexelizumab (Anti-C5 Complement); MEDI-524 (Numax®); Lucentis® (Ranibizumab); Edrecolomab (Panorex®); Trabio® (lerdelimumab); TheraCim hR3 (Nimotuzumab); Omnitarg (Pertuzumab, 2C4); Osidem® (IDM-I); OvaRex® (B43.13); Nuvion® (visilizumab); Cantuzumab mertansine (huC242-DM1); NeoRecormon® (Epoetin beta); Neumega® (Oprelvekin); Neulasta® (Pegylated filgastrim, pegylated G-CSF, pegylated hu-Met-G-CSF); Neupogen® (Filgrastim); Orthoclone OKT3® (Muromonab-CD3); Procrit® (Epoetin alfa); Remicade® (Infliximab), Reopro® (Abciximab), Actemra® (anti-IL6 Receptor mAb), Avastin® (Bevacizumab), HuMax-CD4 (zanolimumab), Rituxan® (Rituximab); Tarceva® (Erlotinib); Roferon-A®-(Interferon alfa-2a); Simulect® (Basiliximab); Stelara™ (Ustekinumab); Prexige® (lumiracoxib); Synagis® (Palivizumab); 146B7-CHO (anti-IL15 antibody, see U.S. Pat. No. 7,153,507), Tysabri® (Natalizumab); Valortim® (MDX-1303, anti-B. anthracis Protective Antigen mAb); ABthrax™; Vectibix® (Panitumumab); Xolair® (Omalizumab), ETI211 (anti-MRSA mAb), IL-I Trap (the Fc portion of human IgG1 and the extracellular domains of both IL-I receptor components (the Type I receptor and receptor accessory protein)), VEGF Trap (Ig domains of VEGFR1 fused to IgG1 Fc), Zenapax® (Daclizumab); Zenapax® (Daclizumab), Zevalin® (Ibritumomab tiuxetan), Zetia (ezetimibe), Atacicept (TACI-Ig), anti-α4β7 mAb (vedolizumab); galiximab (anti-CD80 monoclonal antibody), anti-CD23 mAb (lumiliximab); BR2-Fc (huBR3/huFc fusion protein, soluble BAFF antagonist); Simponi™ (Golimumab); Mapatumumab (human anti-TRAIL Receptor-1 mAb); Ocrelizumab (anti-CD20 human mAb); HuMax-EGFR (zalutumumab); M200 (Volociximab, anti-α5β1 integrin mAb); MDX-010 (Ipilimumab, anti-CTLA-4 mAb and VEGFR-I (IMC-18F1); anti-BR3 mAb; anti-C. difficile Toxin A and Toxin B C mAbs MDX-066 (CDA-I) and MDX-1388); anti-CD22 dsFv-PE38 conjugates (CAT-3888 and CAT-8015); anti-CD25 mAb (HuMax-TAC); anti-TSLP antibodies; anti-TSLP receptor antibody (U.S. Pat. No. 8,101,182); anti-TSLP antibody designated as A5 (U.S. Pat. No. 7,982,016); (anti-CD3 mAb (NI-0401); Adecatumumab (MT201, anti-EpCAM-CD326 mAb); MDX-060, SGN-30, SGN-35 (anti-CD30 mAbs); MDX-1333 (anti-IFNAR); HuMax CD38 (anti-CD38 mAb); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-sclerostin antibodies (see, U.S. Pat. No. 8,715,663 or 7,592,429) anti-sclerostin antibody designated as Ab-5 (U.S. Pat. No. 8,715,663 or 7,592,429); anti-ganglioside GM2 mAb; anti-GDF-8 human mAb (MYO-029); anti-GM-CSF Receptor mAb (CAM-3001); anti-HepC mAb (HuMax HepC); MEDI-545, MDX-1103 (anti-IFNα mAb); anti-IGFIR mAb; anti-IGF-IR mAb (HuMax-Inflam); anti-IL12/IL23p40 mAb (Briakinumab); anti-IL-23p19 mAb (LY2525623); anti-IL13 mAb (CAT-354); anti-IL-17 mAb (AIN457); anti-IL2Ra mAb (HuMax-TAC); anti-IL5 Receptor mAb; anti-integrin receptors mAb (MDX-018, CNTO 95); anti-IPIO Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1 106 (ONO— 4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); and an amyloid-beta monoclonal antibody comprising sequences, SEQ ID NO:8 and SEQ ID NO:6 (U.S. Pat. No. 7,906,625).

Examples of antibodies suitable for the methods and pharmaceutical formulations include the antibodies shown in Table 1. Other examples of suitable antibodies include infliximab, bevacizumab, cetuximab, ranibizumab, palivizumab, abagovomab, abciximab, actoxumab, adalimumab, afelimomab, afutuzumab, alacizumab, alacizumab pegol, ald518, alemtuzumab, alirocumab, altumomab, amatuximab, anatumomab mafenatox, anrukinzumab, apolizumab, arcitumomab, aselizumab, altinumab, atlizumab, atorolimiumab, tocilizumab, bapineuzumab, basiliximab, bavituximab, bectumomab, belimumab, benralizumab, bertilimumab, besilesomab, bevacizumab, bezlotoxumab, biciromab, bivatuzumab, bivatuzumab mertansine, blinatumomab, blosozumab, brentuximab vedotin, briakinumab, brodalumab, canakinumab, cantuzumab mertansine, cantuzumab mertansine, caplacizumab, capromab pendetide, carlumab, catumaxomab, cc49, cedelizumab, certolizumab pegol, cetuximab, citatuzumab bogatox, cixutumumab, clazakizumab, clenoliximab, clivatuzumab tetraxetan, conatumumab, crenezumab, cr6261, dacetuzumab, daclizumab, dalotuzumab, daratumumab, demcizumab, denosumab, detumomab, dorlimomab aritox, drozitumab, duligotumab, dupilumab, ecromeximab, eculizumab, edobacomab, edrecolomab, efalizumab, efungumab, elotuzumab, elsilimomab, enavatuzumab, enlimomab pegol, enokizumab, enoticumab, ensituximab, epitumomab cituxetan, epratuzumab, erenumab, erlizumab, ertumaxomab, etaracizumab, etrolizumab, evolocumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, gs6624, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lebrikizumab, lemalesomab, lerdelimumab, lexatumumab, libivirumab, ligelizumab, lintuzumab, lirilumab, lorvotuzumab mertansine, lucatumumab, lumiliximab, mapatumumab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pintumomab, placulumab, ponezumab, priliximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, tefibazumab, teneliximab, teplizumab, teprotumumab, tezepelumab, TGN1412, tremelimumab, ticilimumab, tildrakizumab, tigatuzumab, TNX-650, tocilizumab, toralizumab, tositumomab, tralokinumab, trastuzumab, TRBS07, tregalizumab, tucotuzumab celmoleukin, tuvirumab, ublituximab, urelumab, urtoxazumab, ustekinumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox.

Antibodies also include adalimumab, bevacizumab, blinatumomab, cetuximab, conatumumab, denosumab, eculizumab, erenumab, evolocumab, infliximab, natalizumab, panitumumab, rilotumumab, rituximab, romosozumab, tezepelumab, and trastuzumab, and antibodies selected from Table 1.

TABLE 1

Examples of therapeutic antibodies

| Target (informal name) | Conc. (mg/ml) | Viscosity (cP) | HC Type (including allotypes) | LC Type | pI | LC SEQ ID NO | HC SEQ ID NO |
|---|---|---|---|---|---|---|---|
| anti-amyloid | 142.2 | 5.0 | IgG1 (f) (R; EM) | Kappa | 9.0 | 1 | 2 |
| GMCSF (247) | 139.7 | 5.6 | IgG2 | Kappa | 8.7 | 3 | 4 |
| CGRPR | 136.6 | 6.3 | IgG2 | Lambda | 8.6 | 5 | 6 |
| RANKL | 152.7 | 6.6 | IgG2 | Kappa | 8.6 | 7 | 8 |
| Sclerostin (27H6) | 145.0 | 6.7 | IgG2 | Kappa | 6.6 | 9 | 10 |
| IL-1R1 | 153.9 | 6.7 | IgG2 | Kappa | 7.4 | 11 | 12 |
| Myostatin | 141.0 | 6.8 | IgG1 (z) (K; EM) | Kappa | 8.7 | 13 | 14 |
| B7RP1 | 137.5 | 7.7 | IgG2 | Kappa | 7.7 | 15 | 16 |
| Amyloid | 140.6 | 8.2 | IgG1 (za) (K; DL) | Kappa | 8.7 | 17 | 18 |
| GMCSF (3.112) | 156.0 | 8.2 | IgG2 | Kappa | 8.8 | 19 | 20 |
| CGRP (32H7) | 159.5 | 8.3 | IgG2 | Kappa | 8.7 | 21 | 22 |
| CGRP (3B6.2) | 161.1 | 8.4 | IgG2 | Lambda | 8.6 | 23 | 24 |
| PCSK9 (8A3.1) | 150.0 | 9.1 | IgG2 | Kappa | 6.7 | 25 | 26 |
| PCSK9 (492) | 150.0 | 9.2 | IgG2 | Kappa | 6.9 | 27 | 28 |
| CGRP | 155.2 | 9.6 | IgG2 | Lambda | 8.8 | 29 | 30 |
| Hepcidin | 147.1 | 9.9 | IgG2 | Lambda | 7.3 | 31 | 32 |
| TNFR p55) | 157.0 | 10.0 | IgG2 | Kappa | 8.2 | 33 | 34 |
| OX40L | 144.5 | 10.0 | IgG2 | Kappa | 8.7 | 35 | 36 |
| HGF | 155.8 | 10.6 | IgG2 | Kappa | 8.1 | 37 | 38 |
| GMCSF | 162.5 | 11.0 | IgG2 | Kappa | 8.1 | 39 | 40 |
| Glucagon R | 146.0 | 12.1 | IgG2 | Kappa | 8.4 | 41 | 42 |
| GMCSF (4.381) | 144.5 | 12.1 | IgG2 | Kappa | 8.4 | 43 | 44 |
| Sclerostin (13F3) | 155.0 | 12.1 | IgG2 | Kappa | 7.8 | 45 | 46 |
| CD-22 | 143.7 | 12.2 | IgG1 (f) (R; EM) | Kappa | 8.8 | 47 | 48 |
| INFgR | 154.2 | 12.2 | IgG1 (za) (K; DL) | Kappa | 8.8 | 49 | 50 |
| Ang2 | 151.5 | 12.4 | IgG2 | Kappa | 7.4 | 51 | 52 |
| TRAILR2 | 158.3 | 12.5 | IgG1 (f) (R; EM) | Kappa | 8.7 | 53 | 54 |
| EGFR | 141.7 | 14.0 | IgG2 | Kappa | 6.8 | 55 | 56 |
| IL-4R | 145.8 | 15.2 | IgG2 | Kappa | 8.6 | 57 | 58 |
| IL-15 | 149.0 | 16.3 | IgG1 (f) (R; EM) | Kappa | 8.8 | 59 | 60 |
| IGF1R | 159.2 | 17.3 | IgG1 (za) (K; DL) | Kappa | 8.6 | 61 | 62 |
| IL-17R | 150.9 | 19.1 | IgG2 | Kappa | 8.6 | 63 | 64 |
| Dkk1 (6.37.5) | 159.4 | 19.6 | IgG2 | Kappa | 8.2 | 65 | 66 |
| Sclerostin | 134.8 | 20.9 | IgG2 | Kappa | 7.4 | 67 | 68 |
| TSLP | 134.2 | 21.4 | IgG2 | Lambda | 7.2 | 69 | 70 |
| Dkk1 (11H10) | 145.3 | 22.5 | IgG2 | Kappa | 8.2 | 71 | 72 |
| PCSK9 | 145.2 | 22.8 | IgG2 | Lambda | 8.1 | 73 | 74 |
| GIPR (2G10.006) | 150.0 | 23.0 | IgG1 (z) (K; EM) | Kappa | 8.1 | 75 | 76 |
| Activin | 133.9 | 29.4 | IgG2 | Lambda | 7.0 | 77 | 78 |
| Sclerostin (2B8) | 150.0 | 30.0 | IgG2 | Lambda | 6.7 | 79 | 80 |
| Sclerostin | 141.4 | 30.4 | IgG2 | Kappa | 6.8 | 81 | 82 |
| c-fms | 146.9 | 32.1 | IgG2 | Kappa | 6.6 | 83 | 84 |
| α4β7 | 154.9 | 32.7 | IgG2 | Kappa | 6.5 | 85 | 86 |

* An exemplary concentration suitable for patient administration; ᴴHC-antibody heavy chain; ᴸLC-antibody light chain.

Based on the foregoing description, it should be appreciated that the devices, systems, and methods described herein facilitate the performance of an assay of a sample substantially in real-time. Thus, the assay can be performed, and the desired result obtained, much more quickly than allowed by conventional processes.

It should also be appreciated that the devices, systems, and methods described herein allow the process of preparing the online, real-time assay using the system 100 to be easily monitored, which can in turn mitigate risk and extend a production run of the product. In particular, this process can be monitored by determining, e.g., using a controller such as the controller 132 and/or manually by an operator of the system 100, whether conditions in the system 100 are optimal, i.e., whether they satisfy a pre-determined performance threshold. As illustrated in FIGS. 3B and 3C, for example, MS Peak Height, expressed in ion counts, for the four reference peptides RP1, RP2, RP3, and RP4 can be obtained and compared against historical values for those reference peptides during the method qualification to determine whether conditions in the system 100 are optimal (and they are), such that the production run can be commenced, continued, or extended. However, when it is determined that the conditions in the system 100 are not optimal, at least one cell culture component can be adjusted until the conditions in the closed system are optimal. Examples of cell culture components that can be adjusted include, but are not limited to: pH, pressure, temperature, media flow (e.g., media flow rate, media feed rate), media content (including amino acids, nutrients, sugars, buffer), gassing strategy (e.g., mix of oxygen and carbon dioxide, gas rate), agitation (e.g., agitation rate), additives (e.g., metal additives, sugar additives), additive (e.g., anti-foam) feed rate, and perfusion rate. In some cases, only one cell culture component may need to be adjusted so that the conditions in the closed system are optimal, while in other cases, multiple cell culture components may need to be adjusted. Alternatively, when it is determined that the conditions are not optimal, or when the conditions in the system 100 are not optimal even after adjusting the at least one cell culture component, the controller and/or the operator of the system 100 may shut down the system 100.

In this manner, the devices, systems, and methods described herein also mitigate risk involved in the continued operation of the system 100 when conditions are not optimal or when it is otherwise undesirable to continue operation of the system 100. In particular, risk can be mitigated by determining (e.g., calculating or obtaining) process parameter and product quality data, e.g., pH, temperature, oxygen dissolution, cell viability, cell density, titer, aggregation, charge variant, glycosylation, etc., associated with the current operation of the system 100, determining whether the process parameter and product quality data satisfy a pre-determined risk threshold (determined before operation of the system 100 by a controller such as the controller 132 and/or responsive to input from the operator of the system 100), and then determining whether to continue, cease, or adjust operation of the system 100 based upon whether the process parameter and product quality data satisfy the pre-determined risk threshold. The pre-determined risk threshold may, for example, be determined by looking at (1) applying available process parameter data and product quality data to calculate average historical multi-variate (MV) data associated with the previous operation of the system 100 or some other similar system, and then (2) establishing the calculated average historical MV data as the threshold (the threshold may be calculated average historical MV data itself or some value or set of values based on the calculated average historical MV data. In one example, the pre-determined risk threshold may represent an acceptable deviation (e.g., three standard deviations) from the calculated average historical MV data. Alternatively or additionally, the pre-determined risk threshold may be determined based upon input from the operator of the system 100. In some cases, the system 100 may be shut down when the process parameter and product quality data associated with the current operation of the system 100 do not satisfy (e.g., exceed) the pre-determined risk threshold. In other cases, however, the system 100 may be adjusted when the process parameter and product quality data associated with the current operation of the system 100 do not satisfy (e.g., exceed) the pre-determined risk threshold or even when the process parameter and product quality data satisfy but are close to the pre-determined risk threshold.

Further, the Applicant has discovered that the devices, systems, and methods described herein also allow production runs using the system 100 to be extended. Conventional processes typically allow for 32 to 40-day production runs, at most. However, the Applicant has found that the devices, systems, and methods described herein allow for 50-80 if not 100 population doublings, i.e., approximately 50-80 if not 100 day production runs. Thus, more product can be obtained, all while operation of the system 100 is monitored to ensure that the product satisfies quality objectives and risk is mitigated.

Preferred embodiments of this disclosure are described herein, including the best mode or modes known to the inventors for carrying out the disclosure. Although numerous examples are shown and described herein, those of skill in the art will readily understand that details of the various embodiments need not be mutually exclusive. Instead, those of skill in the art upon reading the teachings herein should be able to combine one or more features of one embodiment with one or more features of the remaining embodiments. Further, it also should be understood that the illustrated embodiments are exemplary only, and should not be taken as limiting the scope of the disclosure. All methods described herein can be performed in any suitable order unless otherwise indicated herein or otherwise clearly contradicted by context. The use of any and all examples, or exemplary language (e.g., "such as") provided herein, is intended merely to better illuminate the aspects of the exemplary embodiment or embodiments of the disclosure, and do not pose a limitation on the scope of the disclosure. No language in the specification should be construed as indicating any non-claimed element as essential to the practice of the disclosure.

What is claimed is:

1. A method for performing a real-time assay, the method comprising the steps of:
   (a) moving a sample of a product containing therapeutic polypeptides to a polypeptide-binding column via a first holding coil, wherein a single multi-port valve is fluidly coupled to and located downstream of the first holding coil, and the polypeptide-binding column is fluidly coupled to the multi-port valve, and wherein the therapeutic polypeptides are selected from antibodies, antigen-binding fragments of an antibody, and fusion polypeptides;
   (b) binding the therapeutic polypeptides in the sample to the polypeptide binding column, thereby separating the therapeutic polypeptides in the sample from a remainder of the sample;

(c) moving, via the single multi-port valve, an elution buffer solution from a buffer source to the polypeptide binding column, via the first holding coil, and through a second holding coil downstream of the polypeptide binding column, thereby eluting therapeutic polypeptides bound to the polypeptide binding column and moving an elution/polypeptide mixture comprising the elution buffer solution and the eluted polypeptides to the second holding coil;

(d) moving the elution/polypeptide mixture from the second holding coil to a reaction chamber via the single multi-port valve;

(e) incubating the therapeutic polypeptides in the elution/polypeptide mixture in the reaction chamber, resulting in denatured therapeutic polypeptides;

(f) moving a reducing reagent that cleaves disulfide bond crosslinks to the reaction chamber via the first holding coil and via the single multi-port valve after (e);

(g) incubating the denatured therapeutic polypeptides with the reducing reagent in the reaction chamber, resulting in denatured and reduced therapeutic polypeptides;

(h) moving an alkylating reagent that alkylates sulfhydryls to the reaction chamber after (g);

(i) incubating the denatured and reduced therapeutic polypeptides with the alkylating reagent in the reaction chamber, thereby alkylating the denatured and reduced therapeutic polypeptides;

(j) moving the denatured, reduced, and alkylated therapeutic polypeptides, the elution buffer solution, the reducing reagent, and the alkylating reagent from the reaction chamber to a desalting column via the single multi-port valve and the first holding coil, the desalting column equilibrated with a proteolysis buffer;

(k) applying the denatured, reduced, and alkylated therapeutic polypeptides to the desalting column, thereby separating the denatured, reduced, and alkylated therapeutic polypeptides from the reducing and alkylating reagents, and resulting in desalted therapeutic polypeptides;

(l) moving the desalted therapeutic polypeptides to a proteolytic enzyme column downstream of the desalting column;

(m) digesting the desalted therapeutic polypeptides in the proteolytic enzyme column, resulting in digested polypeptides; and (n) moving the digested therapeutic polypeptides to an analytical device for analysis of the digested polypeptides.

2. The method of claim 1, wherein one or more of (a), (c), (d), (f), (h), (i), (l), and (n) are performed automatically.

3. The method of claim 1, wherein (a) through (n) are performed in a closed system.

4. The method of claim 1, further comprising:
prior to or during (d), moving a first valve fluidly coupled to and located downstream of the reaction chamber to a first position in which the first valve directs contents received from the first holding coil in excess of a volume of the reaction chamber to a waste chamber; and
after (i), moving the first valve from the first position to a second position in which the first valve directs air into the reaction chamber.

5. The method of claim 4, further comprising, after (k) and before (l), (o) moving a second valve fluidly coupled to and located between the desalting and proteolytic enzyme columns from a first position, in which the second valve directs contents received from the desalting column to a waste chamber, to a second position, in which the second valve directs contents received from the desalting column to the proteolytic enzyme column.

6. The method of claim 1, wherein the therapeutic polypeptide is an antibody selected from the group consisting of infliximab, bevacizumab, ranibizumab, cetuximab, ranibizumab, palivizumab, abagovomab, abciximab, actoxumab, adalimumab, afelimomab, afutuzumab, alacizumab, alacizumab pegol, ald518, alemtuzumab, alirocumab, alemtuzumab, altumomab, amatuximab, anatumomab mafenatox, anrukinzumab, apolizumab, arcitumomab, aselizumab, altinumab, atlizumab, atorolimiumab, tocilizumab, bapineuzumab, basiliximab, bavituximab, bectumomab, belimumab, benralizumab, bertilimumab, besilesomab, bevacizumab, bezlotoxumab, biciromab, bivatuzumab, bivatuzumab mertansine, blinatumomab, blosozumab, brentuximab vedotin, briakinumab, brodalumab, canakinumab, cantuzumab mertansine, cantuzumab mertansine, caplacizumab, capromab pendetide, carlumab, catumaxomab, cc49, cedelizumab, certolizumab pegol, cetuximab, citatuzumab bogatox, cixutumumab, clazakizumab, clenoliximab, clivatuzumab tetraxetan, conatumumab, crenezumab, cr6261, dacetuzumab, daclizumab, dalotuzumab, daratumumab, demcizumab, denosumab, detumomab, dorlimomab aritox, drozitumab, duligotumab, dupilumab, ecromeximab, eculizumab, edobacomab, edrecolomab, efalizumab, efungumab, elotuzumab, elsilimomab, enavatuzumab, enlimomab pegol, enokizumab, enokizumab, enoticumab, enoticumab, ensituximab, epitumomab cituxetan, epratuzumab, erlizumab, ertumaxomab, etaracizumab, etrolizumab, exbivirumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, gs6624, ibalizumab, ibritumomab tiuxetan, icrucumab, igovomab, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lebrikizumab, lemalesomab, lerdelimumab, lexatumumab, libivirumab, ligelizumab, lintuzumab, lirilumab, lorvotuzumab mertansine, lucatumumab, lumiliximab, mapatumumab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, oportuzumab monatox, oregovomab, orticumab, otelixizumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pintumomab, placulumab, ponezumab, priliximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, tefibazumab, telimomab aritox, tenatumomab, teneliximab, teplizumab, teprotumumab, tezepelumab, TGN1412, tremelimumab, ticilimumab, tildrakizumab, tigatuzumab, TNX-650, tocilizumab, toralizumab, tositumomab, tralokinumab, trastuzumab, TRBS07, tregalizumab, tremelimumab, tucotuzumab celmoleukin, tuvirumab, ublituximab, urelumab, urtoxazumab, ustekinumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, and zolimomab aritox.

\* \* \* \* \*

SEQUENCE LISTING

<160> NUMBER OF SEQ ID NOS: 86

<210> SEQ ID NO 1
<211> LENGTH: 239
<212> TYPE: PRT
<213> ORGANISM: Homo sapiens

<400> SEQUENCE: 1

Met Arg Leu Pro Ala Gln Leu Gly Leu Leu Met Leu Trp Val Pro
1               5                   10                  15

Gly Ser Ser Gly Asp Ile Val Met Thr Gln Thr Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60

Pro Gly Gln Pro Pro Arg Leu Leu Ile Tyr Lys Ile Ser Asn Arg Phe
65                  70                  75                  80

Ser Gly Val Pro Asp Arg Phe Thr Gly Ser Gly Ala Gly Thr Asp Phe
                85                  90                  95

Thr Leu Lys Ile Ser Arg Val Glu Ala Glu Asp Val Gly Val Tyr Thr
            100                 105                 110

Cys Met Gln Val Thr Gln Phe Pro Leu Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 2
<211> LENGTH: 470
<212> TYPE: PRT
<213> ORGANISM: Homo sapiens

<400> SEQUENCE: 2

Met Asp Thr Leu Cys Tyr Thr Leu Leu Leu Thr Thr Pro Ser Trp
1               5                   10                  15

Val Leu Ser Gln Val Thr Leu Lys Glu Ser Gly Pro Val Leu Leu Lys
            20                  25                  30

Pro Thr Glu Thr Leu Thr Leu Thr Cys Thr Val Ser Gly Phe Ser Leu
        35                  40                  45

Ser Asn Ala Arg Met Gly Val Ser Trp Ile Arg Gln Pro Pro Gly Lys
    50                  55                  60

Ala Leu Glu Trp Leu Ala His Ile Phe Ser Asn Asp Glu Lys Ser Tyr
65                  70                  75                  80

Ile Thr Ser Leu Lys Ser Arg Leu Thr Ile Ser Lys Asp Thr Ser Lys
                85                  90                  95

Ser Gln Val Val Leu Thr Met Thr Asn Met Asp Pro Val Asp Thr Ala
            100                 105                 110

Thr Tyr Tyr Cys Ala Arg Ile Pro Leu Arg Ser Pro Gly Ala Phe Asp
        115                 120                 125

Ile Trp Gly Gln Gly Thr Met Val Thr Val Ser Ser Ala Ser Thr Lys

```
                130                 135                 140
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 3
<211> LENGTH: 235
<212> TYPE: PRT
<213> ORGANISM: Homo sapiens

<400> SEQUENCE: 3

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30
```

```
Leu Ser Pro Gly Asp Arg Ala Thr Leu Ser Cys Arg Ala Ser Gln Ser
            35                  40                  45

Val Ser Ser Tyr Phe Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
                100                 105                 110

Asp Arg Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 4
<211> LENGTH: 463
<212> TYPE: PRT
<213> ORGANISM: Homo sapiens

<400> SEQUENCE: 4

Met Asp Trp Thr Trp Arg Ile Leu Phe Leu Val Ala Ala Thr Gly
 1               5                  10                  15

Ala His Ser Gln Val Gln Leu Val Gln Ser Gly Ala Glu Val Lys Lys
                 20                  25                  30

Pro Gly Ala Ser Val Lys Val Ser Cys Lys Ser Ser Gly Tyr Thr Phe
            35                  40                  45

Thr Gly Tyr Tyr Met His Trp Val Arg Gln Ala Pro Gly Gln Gly Leu
 50                  55                  60

Glu Trp Met Gly Trp Ile Asn Pro Asn Ser Gly Gly Thr Asn Tyr Ala
 65                  70                  75                  80

Gln Lys Phe Lys Gly Arg Val Thr Met Thr Arg Asp Thr Ser Ile Ser
                 85                  90                  95

Thr Ala Tyr Met Glu Leu Ser Arg Leu Arg Ser Asp Asp Thr Ala Val
                100                 105                 110

Tyr Tyr Cys Ala Arg Asp Lys Trp Leu Asp Gly Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175
```

-continued

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
            275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460

<210> SEQ ID NO 5
<211> LENGTH: 235
<212> TYPE: PRT
<213> ORGANISM: Homo sapiens

<400> SEQUENCE: 5

Met Ala Trp Ala Leu Leu Leu Thr Leu Leu Thr Gln Asp Thr Gly
1               5                   10                  15

Ser Trp Ala Gln Ser Val Leu Thr Gln Ser Pro Ser Ala Ser Gly Thr
            20                  25                  30

Pro Gly Gln Arg Val Thr Ile Ser Cys Ser Gly Ser Ser Ser Asn Ile
            35                  40                  45

Gly Ser Asn Tyr Val Tyr Trp Tyr Gln Gln Leu Pro Gly Ala Ala Pro
    50                  55                  60

Lys Leu Leu Ile Leu Arg Asn Asn Gln Arg Pro Ser Gly Val Pro Asp
65                  70                  75                  80

Arg Phe Ser Gly Ser Lys Ser Gly Thr Ser Ala Ser Leu Thr Ile Ser

```
            85                  90                  95
Gly Leu Arg Ser Glu Asp Glu Ala Asp Tyr Tyr Cys Ala Ala Trp Asp
            100                 105                 110

Asp Ser Leu Ser Gly Trp Val Phe Gly Gly Thr Lys Leu Thr Val
            115                 120                 125

Leu Gly Gln Pro Lys Ala Asn Pro Thr Val Thr Leu Phe Pro Pro Ser
            130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
                180                 185                 190

Asn Lys Tyr Ala Ala Ser Ser Tyr Leu Ser Leu Thr Pro Glu Gln Trp
                195                 200                 205

Lys Ser His Arg Ser Tyr Ser Cys Gln Val Thr His Glu Gly Ser Thr
                210                 215                 220

Val Glu Lys Thr Val Ala Pro Thr Glu Cys Ser
225                 230                 235

<210> SEQ ID NO 6
<211> LENGTH: 479
<212> TYPE: PRT
<213> ORGANISM: Homo sapiens

<400> SEQUENCE: 6

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Lys Pro Gly Gly Ser Leu Arg Leu Ser Cys Ala Ala Ser Gly
            35                  40                  45

Phe Thr Phe Ser Asn Ala Trp Met Ser Trp Val Arg Gln Ala Pro Gly
        50                  55                  60

Lys Gly Leu Glu Trp Val Gly Arg Ile Lys Ser Lys Thr Asp Gly Gly
65              70                  75                  80

Thr Thr Asp Tyr Thr Ala Pro Val Lys Gly Arg Phe Thr Ile Ser Arg
                85                  90                  95

Asp Asp Ser Lys Asn Thr Leu Tyr Leu Gln Met Asn Ser Leu Lys Ala
            100                 105                 110

Glu Asp Thr Ala Val Tyr Tyr Cys Thr Thr Asp Arg Thr Gly Tyr Ser
        115                 120                 125

Ile Ser Trp Ser Tyr Tyr Tyr Tyr Gly Met Asp Val Trp Gly
        130                 135                 140

Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
                165                 170                 175

Ala Leu Gly Cys Leu Val Lys Asp Tyr Phe Pro Glu Pro Val Thr Val
                180                 185                 190

Ser Trp Asn Ser Gly Ala Leu Thr Ser Gly Val His Thr Phe Pro Ala
            195                 200                 205

Val Leu Gln Ser Ser Gly Leu Tyr Ser Leu Ser Ser Val Val Thr Val
210                 215                 220
```

```
Pro Ser Ser Asn Phe Gly Thr Gln Thr Tyr Thr Cys Asn Val Asp His
225                 230                 235                 240

Lys Pro Ser Asn Thr Lys Val Asp Lys Thr Val Glu Arg Lys Cys Cys
                245                 250                 255

Val Glu Cys Pro Pro Cys Pro Ala Pro Pro Val Ala Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
                325                 330                 335

Val Leu Thr Val Val His Gln Asp Trp Leu Asn Gly Lys Glu Tyr Lys
            340                 345                 350

Cys Lys Val Ser Asn Lys Gly Leu Pro Ala Pro Ile Glu Lys Thr Ile
        355                 360                 365

Ser Lys Thr Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Met Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 7
<211> LENGTH: 235
<212> TYPE: PRT
<213> ORGANISM: Homo sapiens

<400> SEQUENCE: 7

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Arg Gly Arg Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
        115                 120                 125
```

```
Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 8
<211> LENGTH: 467
<212> TYPE: PRT
<213> ORGANISM: Homo sapiens

<400> SEQUENCE: 8

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
```

```
            260                 265                 270
Ile Ser Arg Thr Pro Glu Val Thr Cys Val Val Asp Val Ser His
            275                 280                 285
Glu Asp Pro Glu Val Gln Phe Asn Trp Tyr Val Asp Gly Val Glu Val
            290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
            355                 360                 365
Tyr Thr Leu Pro Pro Ser Arg Glu Glu Met Thr Lys Asn Gln Val Ser
            370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
            450                 455                 460
Pro Gly Lys
465

<210> SEQ ID NO 9
<211> LENGTH: 242
<212> TYPE: PRT
<213> ORGANISM: Homo sapiens

<400> SEQUENCE: 9

Met Asp Met Arg Val Pro Ala Gln Leu Leu Gly Leu Leu Leu Leu Trp
1               5                   10                  15
Leu Arg Gly Ala Arg Cys Asp Ile Val Met Thr Gln Thr Pro Leu Ser
            20                  25                  30
Leu Pro Val Thr Pro Gly Glu Pro Ala Ser Ile Ser Cys Arg Ser Ser
            35                  40                  45
Gln Ser Leu Leu Asn Ser Val Asp Gly Ser Thr Asn Leu Asp Trp Tyr
    50                  55                  60
Leu Gln Lys Pro Gly Gln Ser Pro Gln Leu Leu Ile Tyr Thr Leu Ser
65                  70                  75                  80
Tyr Arg Ala Ser Gly Val Pro Asp Arg Phe Ser Gly Ser Gly Ser Gly
                85                  90                  95
Thr Asp Phe Thr Leu Lys Ile Ser Arg Val Glu Ala Glu Asp Val Gly
            100                 105                 110
Val Tyr Tyr Cys Met Gln Arg Ile Glu Phe Pro Leu Thr Phe Gly Gly
            115                 120                 125
Gly Thr Lys Val Glu Ile Lys Arg Thr Val Ala Ala Pro Ser Val Phe
            130                 135                 140
Ile Phe Pro Pro Ser Asp Glu Gln Leu Lys Ser Gly Thr Ala Ser Val
145                 150                 155                 160
```

```
Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
            195                 200                 205

Leu Ser Lys Ala Asp Tyr Glu Lys His Lys Val Tyr Ala Cys Glu Val
        210                 215                 220

Thr His Gln Gly Leu Ser Ser Pro Val Thr Lys Ser Phe Asn Arg Gly
225                 230                 235                 240

Glu Cys

<210> SEQ ID NO 10
<211> LENGTH: 465
<212> TYPE: PRT
<213> ORGANISM: Homo sapiens

<400> SEQUENCE: 10

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Tyr Ile Ser Ser Ser Gly Ser Ser Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Arg Glu Arg Tyr Tyr Gly Asp Thr Pro Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285
```

-continued

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val His Gln Asp Trp Leu Asn Gly Lys Glu
                325                 330                 335

Tyr Lys Cys Lys Val Ser Asn Lys Gly Leu Pro Ala Pro Ile Glu Lys
                340                 345                 350

Thr Ile Ser Lys Thr Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys
465

<210> SEQ ID NO 11
<211> LENGTH: 233
<212> TYPE: PRT
<213> ORGANISM: Homo sapiens

<400> SEQUENCE: 11

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Tyr Tyr Cys His Gln Ser Ser Ser
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 12
<211> LENGTH: 463
<212> TYPE: PRT
<213> ORGANISM: Homo sapiens

<400> SEQUENCE: 12

Met Gly Ser Thr Ala Ile Leu Ala Leu Leu Ala Val Leu Gln Gly
1               5                   10                  15

Val Cys Ala Glu Val Gln Leu Met Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Ser Phe His Trp Ile Ala Trp Val Arg Gln Met Pro Gly Lys Gly Leu
    50                  55                  60

Glu Trp Met Gly Ile Ile His Pro Gly Ala Ser Asp Thr Arg Tyr Ser
65                  70                  75                  80

Pro Ser Phe Gln Gly Gln Val Thr Ile Ser Ala Asp Asn Ser Asn Ser
                85                  90                  95

Ala Thr Tyr Leu Gln Trp Ser Ser Leu Lys Ala Ser Asp Thr Ala Met
            100                 105                 110

Tyr Phe Cys Ala Arg Gln Arg Glu Leu Asp Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys

```
                      325                 330                 335
        Cys Lys Val Ser Asn Lys Gly Leu Pro Ala Pro Ile Glu Lys Thr Ile
                    340                 345                 350
        Ser Lys Thr Lys Gly Gln Pro Arg Glu Pro Gln Val Tyr Thr Leu Pro
                    355                 360                 365
        Pro Ser Arg Glu Glu Met Thr Lys Asn Gln Val Ser Leu Thr Cys Leu
            370                 375                 380
        Val Lys Gly Phe Tyr Pro Ser Asp Ile Ala Val Glu Trp Glu Ser Asn
        385                 390                 395                 400
        Gly Gln Pro Glu Asn Asn Tyr Lys Thr Thr Pro Pro Met Leu Asp Ser
                        405                 410                 415
        Asp Gly Ser Phe Phe Leu Tyr Ser Lys Leu Thr Val Asp Lys Ser Arg
                        420                 425                 430
        Trp Gln Gln Gly Asn Val Phe Ser Cys Ser Val Met His Glu Ala Leu
                        435                 440                 445
        His Asn His Tyr Thr Gln Lys Ser Leu Ser Leu Ser Pro Gly Lys
                        450                 455                 460

<210> SEQ ID NO 13
<211> LENGTH: 236
<212> TYPE: PRT
<213> ORGANISM: Homo sapiens

<400> SEQUENCE: 13

Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Ser Ser
                20                  25                  30
Leu Ser Ala Ser Val Gly Asp Arg Val Thr Ile Thr Cys Lys Ala Ser
            35                  40                  45
Gln Asp Ile Asn Lys Tyr Val Ala Trp Tyr Gln Lys Pro Gly Lys
    50                  55                  60
Ala Pro Lys Leu Leu Ile Tyr Tyr Thr Ser Trp Leu Gln Pro Gly Val
65                  70                  75                  80
Pro Ser Arg Phe Ser Gly Ser Gly Ser Gly Thr Asp Phe Thr Phe Thr
                85                  90                  95
Ile Ser Ser Leu Gln Pro Glu Asp Ile Ala Thr Tyr Tyr Cys Leu Gln
            100                 105                 110
Tyr Asp Asn Leu Leu Tyr Thr Phe Gly Gln Gly Thr Lys Leu Glu Ile
        115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

```
<210> SEQ ID NO 14
<211> LENGTH: 467
<212> TYPE: PRT
<213> ORGANISM: Homo sapiens

<400> SEQUENCE: 14

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Arg Tyr Trp Met Asn Trp Val Arg Gln Ala Pro Gly
    50                  55                  60

Lys Gly Leu Glu Trp Val Ala Gln Ile Arg Leu Lys Ser Asp Asn Tyr
65                  70                  75                  80

Ala Thr His Tyr Ala Glu Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Thr Gly Leu Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 15
<211> LENGTH: 236
<212> TYPE: PRT
<213> ORGANISM: Homo sapiens

<400> SEQUENCE: 15

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Asn Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asp Ser Tyr Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 16
<211> LENGTH: 466
<212> TYPE: PRT
<213> ORGANISM: Homo sapiens

<400> SEQUENCE: 16
```

-continued

```
Met Glu Leu Gly Leu Asn Trp Val Phe Leu Val Ala Ile Leu Glu Gly
1               5                   10                  15

Val His Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Tyr Trp Met Ser Trp Val Arg Gln Ala Pro Gly Lys Gly Leu
        50                  55                  60

Glu Trp Val Ala Tyr Ile Lys Gln Asp Gly Asn Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Gly Ile Leu Trp Phe Gly Asp Leu Pro Thr
            115                 120                 125

Phe Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Phe Arg
305                 310                 315                 320

Val Val Ser Val Leu Thr Val His Gln Asp Trp Leu Asn Gly Lys
            325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415
```

```
Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 17
<211> LENGTH: 241
<212> TYPE: PRT
<213> ORGANISM: Homo sapiens

<400> SEQUENCE: 17

Met Asp Met Arg Leu Pro Ala Gln Leu Leu Gly Leu Leu Met Leu Trp
1               5                   10                  15

Val Pro Gly Ser Ser Gly Asp Val Leu Met Thr Gln Ser Pro Leu Ser
            20                  25                  30

Leu Pro Val Thr Leu Gly Gln Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Arg Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Ala Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 18
<211> LENGTH: 470
<212> TYPE: PRT
<213> ORGANISM: Homo sapiens

<400> SEQUENCE: 18

Met Asp Thr Leu Cys Ser Thr Leu Leu Leu Leu Thr Ile Pro Ser Trp
1               5                   10                  15

Val Leu Ser Gln Val Thr Leu Lys Glu Ser Gly Pro Ala Leu Val Lys
```

```
                    20                  25                  30
Pro Thr Gln Thr Leu Thr Leu Thr Cys Thr Phe Ser Gly Phe Ser Leu
                35                  40                  45
Arg Thr Ser Gly Met Gly Val Gly Trp Ile Arg Gln Pro Pro Gly Lys
            50                  55                  60
Ala Leu Glu Trp Leu Ala His Ile Trp Trp Asp Asp Lys Ser Tyr
65                  70                  75                  80
Asn Pro Ser Leu Lys Ser Gln Leu Thr Ile Ser Lys Asp Thr Ser Lys
                85                  90                  95
Asn Gln Val Val Leu Thr Met Thr Asn Met Asp Pro Val Asp Thr Ala
                100                 105                 110
Thr Tyr Tyr Cys Ala Arg Arg Asn Tyr Tyr Asp Tyr Phe Ala
                115                 120                 125
Tyr Trp Gly Gln Gly Thr Leu Val Thr Val Ser Ala Ser Thr Lys
            130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
                195                 200                 205
Val Thr Val Pro Ser Ser Ser Leu Gly Thr Gln Thr Tyr Ile Cys Asn
                210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
                275                 280                 285
Val Ser His Glu Asp Pro Glu Val Lys Phe Asn Trp Tyr Val Asp Gly
            290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
                355                 360                 365
Pro Gln Val Tyr Thr Leu Pro Pro Ser Arg Asp Glu Leu Thr Lys Asn
            370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
                435                 440                 445
```

Ser Val Met His Glu Ala Leu His Asn His Tyr Thr Gln Lys Ser Leu
    450                 455                 460

Ser Leu Ser Pro Gly Lys
465                 470

<210> SEQ ID NO 19
<211> LENGTH: 235
<212> TYPE: PRT
<213> ORGANISM: Homo sapiens

<400> SEQUENCE: 19

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Phe Ala Trp Tyr Gln Gln Lys Pro Gly Gln Ala
    50                  55                  60

Pro Arg Leu Leu Ile Tyr Gly Thr Ser Ser Arg Ala Thr Gly Ile Pro
65                  70                  75                  80

Asp Arg Phe Ser Gly Ser Gly Ser Gly Thr Asp Phe Thr Leu Thr Val
                85                  90                  95

Ser Arg Leu Glu Pro Glu Asp Phe Ala Val Tyr Tyr Cys Gln Gln Tyr
            100                 105                 110

Asp Arg Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 20
<211> LENGTH: 463
<212> TYPE: PRT
<213> ORGANISM: Homo sapiens

<400> SEQUENCE: 20

Met Asp Trp Thr Trp Arg Ile Leu Phe Leu Val Ala Ala Thr Gly
1               5                   10                  15

Ala His Ser Gln Val Gln Leu Val Gln Ser Gly Ala Ala Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Ile His Trp Val Arg Gln Ala Pro Gly Gln Gly Leu
    50                  55                  60

Glu Trp Met Gly Trp Ile Asn Pro Asn Ser Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Ser Met Glu Leu Ser Arg Leu Arg Ser Asp Asp Thr Ala Val
            100                 105                 110

Tyr Phe Cys Ala Arg Asp Arg Trp Leu Asp Ala Phe Asp Ile Trp Gly
        115                 120                 125

Gln Gly Thr Met Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
            290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 21
<211> LENGTH: 235

<212> TYPE: PRT
<213> ORGANISM: Homo sapiens

<400> SEQUENCE: 21

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Gly Tyr Leu Thr Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Asn Ser Leu Ser Arg Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 22
<211> LENGTH: 474
<212> TYPE: PRT
<213> ORGANISM: Homo sapiens

<400> SEQUENCE: 22

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Ile Ile Ser Arg Asp Lys
                85                  90                  95

Ser Lys Asn Thr Leu Tyr Leu Gln Met Asn Ser Leu Arg Ala Glu Asp
            100                 105                 110
```

-continued

```
Thr Ala Val Tyr Tyr Cys Ala Arg Ala Gly Ile Ala Ala Ala Gly
            115                 120                 125
Leu Tyr Tyr Tyr Gly Met Asp Val Trp Gly Gln Gly Thr Thr Val
        130                 135                 140
Thr Val Ser Ser Ala Ser Thr Lys Gly Pro Ser Val Phe Pro Leu Ala
145                 150                 155                 160
Pro Cys Ser Arg Ser Thr Ser Glu Ser Thr Ala Ala Leu Gly Cys Leu
                165                 170                 175
Val Lys Asp Tyr Phe Pro Glu Pro Val Thr Val Ser Trp Asn Ser Gly
                180                 185                 190
Ala Leu Thr Ser Gly Val His Thr Phe Pro Ala Val Leu Gln Ser Ser
            195                 200                 205
Gly Leu Tyr Ser Leu Ser Ser Val Val Thr Val Pro Ser Ser Asn Phe
        210                 215                 220
Gly Thr Gln Thr Tyr Thr Cys Asn Val Asp His Lys Pro Ser Asn Thr
225                 230                 235                 240
Lys Val Asp Lys Thr Val Glu Arg Lys Cys Cys Val Glu Cys Pro Pro
                245                 250                 255
Cys Pro Ala Pro Pro Val Ala Gly Pro Ser Val Phe Leu Phe Pro Pro
                260                 265                 270
Lys Pro Lys Asp Thr Leu Met Ile Ser Arg Thr Pro Glu Val Thr Cys
            275                 280                 285
Val Val Val Asp Val Ser His Glu Asp Pro Glu Val Gln Phe Asn Trp
        290                 295                 300
Tyr Val Asp Gly Val Glu Val His Asn Ala Lys Thr Lys Pro Arg Glu
305                 310                 315                 320
Glu Gln Phe Asn Ser Thr Phe Arg Val Val Ser Val Leu Thr Val Val
                325                 330                 335
His Gln Asp Trp Leu Asn Gly Lys Glu Tyr Lys Cys Lys Val Ser Asn
                340                 345                 350
Lys Gly Leu Pro Ala Pro Ile Glu Lys Thr Ile Ser Lys Thr Lys Gly
            355                 360                 365
Gln Pro Arg Glu Pro Gln Val Tyr Thr Leu Pro Pro Ser Arg Glu Glu
        370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Met Leu Asp Ser Asp Gly Ser Phe Phe
                420                 425                 430
Leu Tyr Ser Lys Leu Thr Val Asp Lys Ser Arg Trp Gln Gln Gly Asn
            435                 440                 445
Val Phe Ser Cys Ser Val Met His Glu Ala Leu His Asn His Tyr Thr
        450                 455                 460
Gln Lys Ser Leu Ser Leu Ser Pro Gly Lys
465                 470

<210> SEQ ID NO 23
<211> LENGTH: 236
<212> TYPE: PRT
<213> ORGANISM: Homo sapiens

<400> SEQUENCE: 23

Met Asp Met Arg Val Pro Ala Gln Leu Leu Gly Leu Leu Leu Leu Trp
1               5                   10                  15
```

-continued

Leu Arg Gly Ala Arg Cys Ser Ser Glu Leu Thr Gln Asp Pro Thr Val
            20                  25                  30

Ser Val Ala Leu Gly Gln Thr Val Lys Ile Thr Cys Gln Gly Asp Ser
        35                  40                  45

Leu Arg Ser Phe Tyr Ala Ser Trp Tyr Gln Gln Lys Pro Gly Gln Ala
50                  55                  60

Pro Val Leu Val Phe Tyr Gly Lys Asn Asn Arg Pro Ser Gly Ile Pro
65                  70                  75                  80

Asp Arg Phe Ser Gly Ser Ser Ser Gly Asn Thr Ala Ser Leu Thr Ile
                85                  90                  95

Thr Gly Ala Gln Ala Glu Asp Glu Ala Asp Tyr Tyr Cys Asn Ser Arg
            100                 105                 110

Asp Ser Ser Val Tyr His Leu Val Leu Gly Gly Gly Thr Lys Leu Thr
        115                 120                 125

Val Leu Gly Gln Pro Lys Ala Asn Pro Thr Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
210                 215                 220

Thr Val Glu Lys Thr Val Ala Pro Thr Glu Cys Ser
225                 230                 235

<210> SEQ ID NO 24
<211> LENGTH: 478
<212> TYPE: PRT
<213> ORGANISM: Homo sapiens

<400> SEQUENCE: 24

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr Tyr Met His Trp Val Arg Gln Ala Pro Gly
50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Phe Cys Ala Arg Asp Gln Met Ser Ile Ile Met Leu
        115                 120                 125

Arg Gly Val Phe Pro Pro Tyr Tyr Tyr Gly Met Asp Val Trp Gly Gln
130                 135                 140

Gly Thr Thr Val Thr Val Ser Ser Ala Ser Thr Lys Gly Pro Ser Val

```
                145                 150                 155                 160
        Phe Pro Leu Ala Pro Cys Ser Arg Ser Thr Ser Glu Ser Thr Ala Ala
                        165                 170                 175

Leu Gly Cys Leu Val Lys Asp Tyr Phe Pro Glu Pro Val Thr Val Ser
                        180                 185                 190

Trp Asn Ser Gly Ala Leu Thr Ser Gly Val His Thr Phe Pro Ala Val
                        195                 200                 205

Leu Gln Ser Ser Gly Leu Tyr Ser Leu Ser Ser Val Val Thr Val Pro
                        210                 215                 220

Ser Ser Asn Phe Gly Thr Gln Thr Tyr Thr Cys Asn Val Asp His Lys
        225                 230                 235                 240

Pro Ser Asn Thr Lys Val Asp Lys Thr Val Glu Arg Lys Cys Cys Val
                        245                 250                 255

Glu Cys Pro Pro Cys Pro Ala Pro Pro Val Ala Gly Pro Ser Val Phe
                        260                 265                 270

Leu Phe Pro Pro Lys Pro Lys Asp Thr Leu Met Ile Ser Arg Thr Pro
                        275                 280                 285

Glu Val Thr Cys Val Val Val Asp Val Ser His Glu Asp Pro Glu Val
                        290                 295                 300

Gln Phe Asn Trp Tyr Val Asp Gly Val Glu Val His Asn Ala Lys Thr
        305                 310                 315                 320

Lys Pro Arg Glu Glu Gln Phe Asn Ser Thr Phe Arg Val Val Ser Val
                        325                 330                 335

Leu Thr Val Val His Gln Asp Trp Leu Asn Gly Lys Glu Tyr Lys Cys
                        340                 345                 350

Lys Val Ser Asn Lys Gly Leu Pro Ala Pro Ile Glu Lys Thr Ile Ser
                        355                 360                 365

Lys Thr Lys Gly Gln Pro Arg Glu Pro Gln Val Tyr Thr Leu Pro Pro
                        370                 375                 380

Ser Arg Glu Glu Met Thr Lys Asn Gln Val Ser Leu Thr Cys Leu Val
        385                 390                 395                 400

Lys Gly Phe Tyr Pro Ser Asp Ile Ala Val Glu Trp Glu Ser Asn Gly
                        405                 410                 415

Gln Pro Glu Asn Asn Tyr Lys Thr Thr Pro Pro Met Leu Asp Ser Asp
                        420                 425                 430

Gly Ser Phe Phe Leu Tyr Ser Lys Leu Thr Val Asp Lys Ser Arg Trp
                        435                 440                 445

Gln Gln Gly Asn Val Phe Ser Cys Ser Val Met His Glu Ala Leu His
                        450                 455                 460

Asn His Tyr Thr Gln Lys Ser Leu Ser Leu Ser Pro Gly Lys
        465                 470                 475

<210> SEQ ID NO 25
<211> LENGTH: 241
<212> TYPE: PRT
<213> ORGANISM: Homo sapiens

<400> SEQUENCE: 25

Met Asp Met Arg Val Pro Ala Gln Leu Leu Gly Leu Leu Leu Leu Trp
        1               5                   10                  15

Leu Arg Gly Ala Arg Cys Asp Ile Val Met Thr Gln Ser Pro Leu Ser
                        20                  25                  30

Leu Pro Val Thr Pro Gly Glu Pro Ala Ser Ile Ser Cys Arg Ser Ser
                        35                  40                  45
```

```
Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Leu Thr Phe Gly Gly Gly
            115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 26
<211> LENGTH: 475
<212> TYPE: PRT
<213> ORGANISM: Homo sapiens

<400> SEQUENCE: 26

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Trp Met Ser Trp Val Arg Gln Ala Pro Gly
    50                  55                  60

Lys Gly Leu Glu Trp Val Ala Ser Ile Lys Gln Asp Gly Ser Glu Lys
65                  70                  75                  80

Tyr Tyr Val Asp Ser Val Lys Gly Arg Phe Thr Ile Ser Arg Asp Asn
                85                  90                  95

Ala Arg Asn Ser Leu Tyr Leu Gln Met Asn Ser Leu Arg Ala Glu Asp
            100                 105                 110

Thr Ala Val Tyr Tyr Cys Ala Arg Asp Leu Val Leu Met Val Tyr Asp
            115                 120                 125

Ile Asp Tyr Tyr Tyr Tyr Gly Met Asp Val Trp Gly Gln Gly Thr Thr
130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175
```

```
Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 27
<211> LENGTH: 241
<212> TYPE: PRT
<213> ORGANISM: Homo sapiens

<400> SEQUENCE: 27

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80
```

```
Arg Ala Ser Gly Val Pro Asp Arg Phe Ser Gly Ser Gly Ser Gly Thr
                85                  90                  95

His Leu Thr Leu Lys Ile Ser Arg Val Glu Ala Glu Asp Val Gly Val
            100                 105                 110

Tyr Tyr Cys Met Gln Thr Leu Gln Thr Pro Leu Thr Phe Gly Gly Gly
        115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 28
<211> LENGTH: 475
<212> TYPE: PRT
<213> ORGANISM: Homo sapiens

<400> SEQUENCE: 28

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Trp Met Ser Trp Val Arg Gln Ala Pro Gly
50                  55                  60

Lys Gly Leu Glu Trp Val Ala Ser Ile Lys Gln Asp Gly Ser Glu Lys
65                  70                  75                  80

Tyr Tyr Val Asp Ser Val Lys Gly Arg Phe Ala Ile Ser Arg Asp Asn
                85                  90                  95

Ala Lys Asn Ser Leu Phe Leu Gln Met Asn Ser Leu Arg Ala Glu Asp
            100                 105                 110

Thr Ala Val Tyr Tyr Cys Ala Arg Asp Leu Val Leu Met Val Tyr Asp
        115                 120                 125

Ile Asp Tyr Tyr Tyr Gly Met Asp Val Trp Gly Gln Gly Thr Thr
130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205
```

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
            245                 250                 255

Pro Cys Pro Ala Pro Pro Val Ala Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 29
<211> LENGTH: 235
<212> TYPE: PRT
<213> ORGANISM: Homo sapiens

<400> SEQUENCE: 29

Met Thr Cys Ser Pro Leu Leu Leu Thr Leu Leu Ile His Cys Thr Gly
1               5                   10                  15

Ser Trp Ala Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Val Ser Trp Tyr Gln Gln Leu Pro Gly Thr Ala Pro
    50                  55                  60

Lys Leu Leu Ile Tyr Asp Asn Asn Lys Arg Pro Ser Gly Ile Pro Asp
65                  70                  75                  80

Arg Phe Ser Gly Ser Lys Ser Gly Thr Ser Thr Leu Gly Ile Thr
                85                  90                  95

Gly Leu Gln Thr Gly Asp Glu Ala Asp Tyr Tyr Cys Gly Thr Trp Asp

```
                    100                 105                 110
Ser Arg Leu Ser Ala Val Val Phe Gly Gly Gly Thr Lys Leu Thr Val
            115                 120                 125
Leu Gly Gln Pro Lys Ala Asn Pro Thr Val Thr Leu Phe Pro Pro Ser
        130                 135                 140
Ser Glu Glu Leu Gln Ala Asn Lys Ala Thr Leu Val Cys Leu Ile Ser
145                 150                 155                 160
Asp Phe Tyr Pro Gly Ala Val Thr Val Ala Trp Lys Ala Asp Gly Ser
                165                 170                 175
Pro Val Lys Ala Gly Val Glu Thr Thr Lys Pro Ser Lys Gln Ser Asn
            180                 185                 190
Asn Lys Tyr Ala Ala Ser Ser Tyr Leu Ser Leu Thr Pro Glu Gln Trp
        195                 200                 205
Lys Ser His Arg Ser Tyr Ser Cys Gln Val Thr His Glu Gly Ser Thr
210                 215                 220
Val Glu Lys Thr Val Ala Pro Thr Glu Cys Ser
225                 230                 235

<210> SEQ ID NO 30
<211> LENGTH: 475
<212> TYPE: PRT
<213> ORGANISM: Homo sapiens

<400> SEQUENCE: 30

Met Glu Phe Gly Leu Ser Trp Val Phe Leu Val Ala Leu Leu Arg Gly
1               5                   10                  15
Val Gln Cys Gln Val Gln Leu Val Glu Ser Gly Gly Gly Val Val Gln
            20                  25                  30
Pro Gly Arg Ser Leu Arg Leu Ser Cys Ala Ala Ser Gly Phe Thr Phe
        35                  40                  45
Ser Ser Phe Gly Met His Trp Val Arg Gln Ala Pro Gly Lys Gly Leu
    50                  55                  60
Glu Trp Val Ala Val Ile Ser Phe Asp Gly Ser Ile Lys Tyr Ser Val
65                  70                  75                  80
Asp Ser Val Lys Gly Arg Phe Thr Ile Ser Arg Asp Asn Ser Lys Asn
                85                  90                  95
Thr Leu Phe Leu Gln Met Asn Ser Leu Arg Ala Glu Asp Thr Ala Val
            100                 105                 110
Tyr Tyr Cys Ala Arg Asp Arg Leu Asn Tyr Tyr Asp Ser Ser Gly Tyr
        115                 120                 125
Tyr His Tyr Lys Tyr Tyr Gly Met Ala Val Trp Gly Gln Gly Thr Thr
    130                 135                 140
Val Thr Val Ser Ser Ala Ser Thr Lys Gly Pro Ser Val Phe Pro Leu
145                 150                 155                 160
Ala Pro Cys Ser Arg Ser Thr Ser Glu Ser Thr Ala Ala Leu Gly Cys
                165                 170                 175
Leu Val Lys Asp Tyr Phe Pro Glu Pro Val Thr Val Ser Trp Asn Ser
            180                 185                 190
Gly Ala Leu Thr Ser Gly Val His Thr Phe Pro Ala Val Leu Gln Ser
        195                 200                 205
Ser Gly Leu Tyr Ser Leu Ser Ser Val Val Thr Val Pro Ser Ser Asn
    210                 215                 220
Phe Gly Thr Gln Thr Tyr Thr Cys Asn Val Asp His Lys Pro Ser Asn
225                 230                 235                 240
```

```
Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Gln Phe Asn
290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
                340                 345                 350

Asn Lys Gly Leu Pro Ala Pro Ile Glu Lys Thr Ile Ser Lys Thr Lys
                355                 360                 365

Gly Gln Pro Arg Glu Pro Gln Val Tyr Thr Leu Pro Pro Ser Arg Glu
            370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
                420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 31
<211> LENGTH: 234
<212> TYPE: PRT
<213> ORGANISM: Homo sapiens

<400> SEQUENCE: 31

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Thr Ile Thr Cys Ser Gly Asp Lys Leu
        35                  40                  45

Gly Glu Arg Tyr Ala Ser Trp Tyr Gln Gln Arg Pro Gly Gln Ser Pro
    50                  55                  60

Val Leu Val Ile Tyr Gln Asp Ile Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Phe Cys Gly Ala Trp Tyr
                100                 105                 110

Ser Ser Thr Asn Val Leu Phe Gly Gly Gly Thr Lys Leu Thr Val Leu
            115                 120                 125

Gly Gln Pro Lys Ala Ala Pro Ser Val Thr Leu Phe Pro Pro Ser Ser
    130                 135                 140
```

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
            165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230

<210> SEQ ID NO 32
<211> LENGTH: 466
<212> TYPE: PRT
<213> ORGANISM: Homo sapiens

<400> SEQUENCE: 32

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Ile Ala Pro Asp Ala Phe Asp
            115                 120                 125

Ile Trp Gly Gln Gly Thr Met Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu

```
                275                 280                 285
Asp Pro Glu Val Gln Phe Asn Trp Tyr Val Asp Gly Val Glu Val His
    290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                325                 330                 335
Glu Tyr Lys Cys Lys Val Ser Asn Lys Gly Leu Pro Ala Pro Ile Glu
            340                 345                 350
Lys Thr Ile Ser Lys Thr Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 33
<211> LENGTH: 234
<212> TYPE: PRT
<213> ORGANISM: Homo sapiens

<400> SEQUENCE: 33

Met Gly Ser Thr Ala Ile Leu Gly Leu Leu Leu Ala Val Leu Gln Gly
1               5                   10                  15
Gly Arg Ala Glu Ile Val Leu Thr Gln Ser Pro Gly Thr Leu Ser Leu
            20                  25                  30
Ser Pro Gly Glu Arg Ala Thr Leu Ser Cys Arg Ala Ser Gln Ser Val
        35                  40                  45
Ser Ser Ser Tyr Leu Ala Trp His Gln Gln Lys Pro Gly Gln Ala Pro
    50                  55                  60
Arg Leu Leu Ile Tyr Gly Ala Ser Ser Arg Ala Thr Gly Ile Pro Asp
65                  70                  75                  80
Arg Phe Ser Gly Ser Gly Ser Gly Thr Asp Phe Thr Leu Thr Ile Ser
                85                  90                  95
Arg Leu Glu Pro Glu Asp Phe Ala Val Tyr Tyr Cys Gln Gln Tyr Gly
            100                 105                 110
Ser Ser Pro Trp Thr Phe Gly Gln Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 34
<211> LENGTH: 463
<212> TYPE: PRT
<213> ORGANISM: Homo sapiens

<400> SEQUENCE: 34

Met Gly Ser Thr Ala Ile Leu Gly Leu Leu Leu Ala Val Leu Gln Gly
1               5                   10                  15

Gly Arg Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Val Met Ser Trp Val Arg Gln Ala Pro Gly Lys Gly Leu
    50                  55                  60

Glu Trp Val Ser Ser Ile Ser Gly Ser Gly Leu Gly Ser Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ala His Arg Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320
```

```
Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
            405                 410                 415

Asp Gly Ser Phe Phe Leu Tyr Ser Lys Leu Thr Val Asp Lys Ser Arg
        420                 425                 430

Trp Gln Gln Gly Asn Val Phe Ser Cys Ser Val Met His Glu Ala Leu
    435                 440                 445

His Asn His Tyr Thr Gln Lys Ser Leu Ser Leu Ser Pro Gly Lys
        450                 455                 460

<210> SEQ ID NO 35
<211> LENGTH: 239
<212> TYPE: PRT
<213> ORGANISM: Homo sapiens

<400> SEQUENCE: 35

Met Arg Leu Leu Ala Gln Leu Leu Gly Leu Leu Met Leu Trp Val Pro
1               5                   10                  15

Gly Ser Ser Gly Asp Ile Val Met Thr Gln Thr Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Ser Trp Leu Gln Gln Arg
    50                  55                  60

Pro Gly Gln Pro Pro Arg Leu Leu Ile Tyr Lys Lys Phe Asn Arg Phe
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Thr Gln Ile Pro Leu Thr Phe Gly Pro Gly Thr Lys
        115                 120                 125

Val Asp Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
```

<210> SEQ ID NO 36
<211> LENGTH: 472
<212> TYPE: PRT
<213> ORGANISM: Homo sapiens

<400> SEQUENCE: 36

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Phe Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Gly Tyr Asp Tyr Val Trp Gly Ser Tyr Arg
        115                 120                 125

Arg Asn Ser Asp Phe Asp Tyr Trp Gly Gln Gly Thr Leu Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350

Leu Pro Ala Pro Ile Glu Lys Thr Ile Ser Lys Thr Lys Gly Gln Pro
        355                 360                 365

```
Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Lys
465                 470

<210> SEQ ID NO 37
<211> LENGTH: 235
<212> TYPE: PRT
<213> ORGANISM: Homo sapiens

<400> SEQUENCE: 37

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Asp Ser Asn Leu Ala Trp Tyr Arg Gln Lys Pro Gly Gln Ala Pro
50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Ile
            100                 105                 110

Asn Trp Pro Pro Ile Thr Phe Gly Gln Gly Thr Arg Leu Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 38
<211> LENGTH: 465
<212> TYPE: PRT
<213> ORGANISM: Homo sapiens
```

<400> SEQUENCE: 38

Met Lys His Leu Trp Phe Phe Leu Leu Val Ala Ala Pro Arg Trp
1               5                   10                  15

Val Leu Ser Gln Val Gln Leu Gln Glu Ser Gly Pro Gly Leu Val Lys
        20                  25                  30

Pro Ser Glu Thr Leu Ser Leu Thr Cys Thr Val Ser Gly Gly Ser Ile
            35                  40                  45

Ser Ile Tyr Tyr Trp Ser Trp Ile Arg Gln Pro Pro Gly Lys Gly Leu
    50                  55                  60

Glu Trp Ile Gly Tyr Val Tyr Tyr Ser Gly Ser Thr Asn Tyr Asn Pro
65              70                  75                  80

Ser Leu Lys Ser Arg Val Thr Ile Ser Val Asp Thr Ser Lys Asn Gln
                85                  90                  95

Phe Ser Leu Lys Leu Asn Ser Val Thr Ala Ala Asp Thr Ala Val Tyr
            100                 105                 110

Tyr Cys Ala Arg Gly Gly Tyr Asp Phe Trp Ser Gly Tyr Phe Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu

```
                    405                 410                 415
Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
        450                 455                 460

Lys
465

<210> SEQ ID NO 39
<211> LENGTH: 240
<212> TYPE: PRT
<213> ORGANISM: Homo sapiens

<400> SEQUENCE: 39

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Ile Leu Tyr Ser Ser Ser Asn Glu Asn Phe Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Pro Glu Asp Val Ala Val Tyr
            100                 105                 110

Tyr Cys Gln Gln Tyr Phe Ser Val Phe Arg Thr Phe Gly Gln Gly Thr
        115                 120                 125

Arg Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 40
<211> LENGTH: 465
<212> TYPE: PRT
<213> ORGANISM: Homo sapiens

<400> SEQUENCE: 40

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
```

```
                   20                  25                  30
Pro Gly Ala Ser Val Lys Val Ser Cys Lys Ala Ser Gly Tyr Thr Phe
               35                  40                  45
Thr Gly Tyr Tyr Ile His Trp Val Arg Gln Ala Pro Gly Gln Gly Leu
           50                  55                  60
Glu Trp Met Gly Trp Ile Asn Pro Asn Ser Gly Thr Asn Ser Ala
65                  70                  75                  80
Gln Lys Phe Arg Gly Arg Val Thr Met Thr Arg Asp Thr Ser Ile Ser
                       85                  90                  95
Thr Ala Tyr Met Glu Leu Ser Arg Leu Arg Ser Asp Thr Ala Val
               100                 105                 110
Tyr Tyr Cys Ala Arg Glu Gly Gly Tyr Ser Tyr Gly Tyr Phe Asp Tyr
               115                 120                 125
Trp Gly Gln Gly Thr Leu Val Thr Val Ser Ser Ala Ser Thr Lys Gly
               130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                   165                 170                 175
Thr Val Ser Trp Asn Ser Gly Ala Leu Thr Ser Gly Val His Thr Phe
                   180                 185                 190
Pro Ala Val Leu Gln Ser Ser Gly Leu Tyr Ser Leu Ser Ser Val Val
               195                 200                 205
Thr Val Pro Ser Ser Asn Phe Gly Thr Gln Thr Tyr Thr Cys Asn Val
               210                 215                 220
Asp His Lys Pro Ser Asn Thr Lys Val Asp Lys Thr Val Glu Arg Lys
225                 230                 235                 240
Cys Cys Val Glu Cys Pro Pro Cys Pro Ala Pro Pro Val Ala Gly Pro
                   245                 250                 255
Ser Val Phe Leu Phe Pro Pro Lys Pro Lys Asp Thr Leu Met Ile Ser
                   260                 265                 270
Arg Thr Pro Glu Val Thr Cys Val Val Val Asp Val Ser His Glu Asp
               275                 280                 285
Pro Glu Val Gln Phe Asn Trp Tyr Val Asp Gly Val Glu Val His Asn
           290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                   325                 330                 335
Tyr Lys Cys Lys Val Ser Asn Lys Gly Leu Pro Ala Pro Ile Glu Lys
                   340                 345                 350
Thr Ile Ser Lys Thr Lys Gly Gln Pro Arg Glu Pro Gln Val Tyr Thr
               355                 360                 365
Leu Pro Pro Ser Arg Glu Glu Met Thr Lys Asn Gln Val Ser Leu Thr
           370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                   405                 410                 415
Asp Ser Asp Gly Ser Phe Phe Leu Tyr Ser Lys Leu Thr Val Asp Lys
                   420                 425                 430
Ser Arg Trp Gln Gln Gly Asn Val Phe Ser Cys Ser Val Met His Glu
               435                 440                 445
```

```
Ala Leu His Asn His Tyr Thr Gln Lys Ser Leu Ser Leu Ser Pro Gly
            450                 455                 460
Lys
465

<210> SEQ ID NO 41
<211> LENGTH: 236
<212> TYPE: PRT
<213> ORGANISM: Homo sapiens

<400> SEQUENCE: 41

Met Asp Met Arg Val Pro Ala Gln Leu Gly Leu Leu Leu Leu Trp
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Tyr Gln Lys Pro Gly Lys
        50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
                100                 105                 110

His Asn Ser Asn Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 42
<211> LENGTH: 473
<212> TYPE: PRT
<213> ORGANISM: Homo sapiens

<400> SEQUENCE: 42

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60
```

-continued

```
Glu Trp Val Ala Val Met Trp Tyr Asp Gly Ser Asn Lys Asp Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Arg Leu Arg Ala Glu Asp Thr Ala Val
            100                 105                 110

Tyr Tyr Cys Ala Arg Glu Lys Asp His Tyr Asp Ile Leu Thr Gly Tyr
        115                 120                 125

Asn Tyr Tyr Gly Leu Asp Val Trp Gly Gln Gly Thr Thr Val Thr
130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365

Pro Arg Glu Pro Gln Val Tyr Thr Leu Pro Pro Ser Arg Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470
```

<210> SEQ ID NO 43
<211> LENGTH: 235
<212> TYPE: PRT
<213> ORGANISM: Homo sapiens

<400> SEQUENCE: 43

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Tyr
            35                  40                  45

Ile Ser Asn Thr Tyr Leu Ala Trp Phe Gln Gln Lys Pro Gly Gln Ala
50                  55                  60

Pro Arg Leu Leu Ile Tyr Gly Ala Ala Thr Arg Ala Thr Gly Ile Pro
65                  70                  75                  80

Asp Arg Phe Ser Gly Ser Gly Ser Gly Thr Asp Phe Thr Phe Thr Ile
            85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Thr Val Glu Ile Lys
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 44
<211> LENGTH: 463
<212> TYPE: PRT
<213> ORGANISM: Homo sapiens

<400> SEQUENCE: 44

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
50                  55                  60

Glu Trp Met Gly Trp Ile Asn Pro Asn Ser Gly Gly Thr Asn Tyr Ala
65                  70                  75                  80

Gln Arg Phe Arg Gly Arg Val Thr Met Thr Arg Asp Thr Ser Ile Ser
            85                  90                  95

-continued

```
Thr Ala Tyr Met Glu Leu Ser Arg Leu Arg Ser Asp Asp Thr Ala Val
                100                 105                 110

Tyr Tyr Cys Ala Arg Ala Pro Tyr Asp Trp Thr Phe Asp Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 45
<211> LENGTH: 236
<212> TYPE: PRT
<213> ORGANISM: Homo sapiens

<400> SEQUENCE: 45

Met Asp Met Arg Val Pro Ala Gln Leu Leu Gly Leu Leu Leu Leu Trp
1               5                   10                  15
```

```
Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Asn Trp Leu Ala Trp Tyr Gln Gln Lys Pro Gly Thr
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 46
<211> LENGTH: 469
<212> TYPE: PRT
<213> ORGANISM: Homo sapiens

<400> SEQUENCE: 46

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Thr Glu
            20                  25                  30

Val Lys Lys Pro Gly Ala Ser Met Lys Val Ser Cys Lys Ala Ser Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Ile Ile Asn Pro Ser Gly Asp Ser Thr
65                  70                  75                  80

Ser Tyr Ala Gln Lys Phe Gln Gly Arg Val Thr Met Thr Arg Asp Thr
                85                  90                  95

Ser Thr Asn Thr Val Tyr Met Glu Leu Ser Ser Leu Arg Ser Glu Asp
            100                 105                 110

Thr Ala Met Tyr Tyr Cys Ala Arg Asp Val Glu Val Arg Gly Ile Ser
        115                 120                 125

His Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
```

```
                    145                 150                 155                 160
            Thr Ser Glu Ser Thr Ala Ala Leu Gly Cys Leu Val Lys Asp Tyr Phe
                            165                 170                 175

Pro Glu Pro Val Thr Val Ser Trp Asn Ser Gly Ala Leu Thr Ser Gly
                            180                 185                 190

Val His Thr Phe Pro Ala Val Leu Gln Ser Ser Gly Leu Tyr Ser Leu
                            195                 200                 205

Ser Ser Val Val Thr Val Pro Ser Ser Asn Phe Gly Thr Gln Thr Tyr
                210                 215                 220

Thr Cys Asn Val Asp His Lys Pro Ser Asn Thr Lys Val Asp Lys Thr
            225                 230                 235                 240

Val Glu Arg Lys Cys Val Glu Cys Pro Cys Pro Ala Pro Pro
                            245                 250                 255

Val Ala Gly Pro Ser Val Phe Leu Phe Pro Pro Lys Pro Lys Asp Thr
                            260                 265                 270

Leu Met Ile Ser Arg Thr Pro Glu Val Thr Cys Val Val Val Asp Val
                            275                 280                 285

Ser His Glu Asp Pro Glu Val Gln Phe Asn Trp Tyr Val Asp Gly Val
                290                 295                 300

Glu Val His Asn Ala Lys Thr Lys Pro Arg Glu Glu Gln Phe Asn Ser
            305                 310                 315                 320

Thr Phe Arg Val Val Ser Val Leu Thr Val Val His Gln Asp Trp Leu
                            325                 330                 335

Asn Gly Lys Glu Tyr Lys Cys Lys Val Ser Asn Lys Gly Leu Pro Ala
                            340                 345                 350

Pro Ile Glu Lys Thr Ile Ser Lys Thr Lys Gly Gln Pro Arg Glu Pro
                            355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
            385                 390                 395                 400

Val Glu Trp Glu Ser Asn Gly Gln Pro Glu Asn Asn Tyr Lys Thr Thr
                            405                 410                 415

Pro Pro Met Leu Asp Ser Asp Gly Ser Phe Phe Leu Tyr Ser Lys Leu
                            420                 425                 430

Thr Val Asp Lys Ser Arg Trp Gln Gln Gly Asn Val Phe Ser Cys Ser
                            435                 440                 445

Val Met His Glu Ala Leu His Asn His Tyr Thr Gln Lys Ser Leu Ser
                450                 455                 460

Leu Ser Pro Gly Lys
            465

<210> SEQ ID NO 47
<211> LENGTH: 238
<212> TYPE: PRT
<213> ORGANISM: Homo sapiens

<400> SEQUENCE: 47

Met Gly Trp Ser Cys Ile Ile Leu Phe Leu Val Ala Thr Ala Thr Gly
            1               5                   10                  15

Val His Ser Asp Ile Gln Leu Thr Gln Ser Pro Ser Ser Leu Ser Ala
                            20                  25                  30

Ser Val Gly Asp Arg Val Thr Met Ser Cys Lys Ser Ser Gln Ser Val
                            35                  40                  45
```

```
Leu Tyr Ser Ala Asn His Lys Asn Tyr Leu Ala Trp Tyr Gln Gln Lys
 50                  55                  60

Pro Gly Lys Ala Pro Lys Leu Leu Ile Tyr Trp Ala Ser Thr Arg Glu
 65                  70                  75                  80

Ser Gly Val Pro Ser Arg Phe Ser Gly Ser Gly Ser Gly Thr Asp Phe
                 85                  90                  95

Thr Phe Thr Ile Ser Ser Leu Gln Pro Glu Asp Ile Ala Thr Tyr Tyr
                100                 105                 110

Cys His Gln Tyr Leu Ser Ser Trp Thr Phe Gly Gly Gly Thr Lys Val
                115                 120                 125

Gln Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 48
<211> LENGTH: 465
<212> TYPE: PRT
<213> ORGANISM: Homo sapiens

<400> SEQUENCE: 48

Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
                 20                  25                  30

Pro Gly Ser Ser Val Lys Val Ser Cys Lys Ala Ser Gly Tyr Thr Phe
                 35                  40                  45

Thr Ser Tyr Trp Leu His Trp Val Arg Gln Ala Pro Gly Gln Gly Leu
 50                  55                  60

Glu Trp Ile Gly Tyr Ile Asn Pro Arg Asn Asp Tyr Thr Glu Tyr Asn
 65                  70                  75                  80

Gln Asn Phe Lys Asp Lys Ala Thr Ile Thr Ala Asp Glu Ser Thr Asn
                 85                  90                  95

Thr Ala Tyr Met Glu Leu Ser Ser Leu Arg Ser Glu Asp Thr Ala Phe
                100                 105                 110

Tyr Phe Cys Ala Arg Arg Asp Ile Thr Thr Phe Tyr Trp Gly Gln Gly
                115                 120                 125

Thr Thr Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190
```

```
Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
        210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
                275                 280                 285

Pro Glu Val Lys Phe Asn Trp Tyr Val Asp Gly Val Glu Val His Asn
        290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Arg Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
        450                 455                 460

Lys
465

<210> SEQ ID NO 49
<211> LENGTH: 235
<212> TYPE: PRT
<213> ORGANISM: Homo sapiens

<400> SEQUENCE: 49

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
        20                  25                  30

Leu Ser Pro Gly Glu Arg Ala Thr Leu Ser Cys Arg Ala Ser Gln Ser
                35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
```

```
                85                  90                  95
Ser Arg Leu Glu Pro Glu Asp Phe Ala Val Tyr Tyr Cys Gln Arg Ser
            100                 105                 110

Gly Gly Ser Ser Phe Thr Phe Gly Pro Gly Thr Lys Val Asp Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 50
<211> LENGTH: 466
<212> TYPE: PRT
<213> ORGANISM: Homo sapiens

<400> SEQUENCE: 50

Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Asn Phe
        35                  40                  45

Thr Ser Tyr Trp Ile Gly Trp Val Arg Gln Met Pro Gly Lys Gly Leu
50                  55                  60

Glu Leu Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Gly Ser Gly Ser Tyr Phe Tyr Phe Asp Leu Trp Gly Arg
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Ser Leu Gly Thr Gln Thr Tyr Ile Cys Asn Val Asn His Lys
            210                 215                 220
```

```
Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 51
<211> LENGTH: 241
<212> TYPE: PRT
<213> ORGANISM: Homo sapiens

<400> SEQUENCE: 51

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser His Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Pro Thr Phe Gly Gln Gly
        115                 120                 125
```

```
Thr Lys Leu Glu Ile Lys Arg Thr Val Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
210                 215                 220

His Gln Gly Leu Ser Ser Pro Val Thr Lys Ser Phe Asn Arg Gly Glu
225                 230                 235                 240

Cys

<210> SEQ ID NO 52
<211> LENGTH: 470
<212> TYPE: PRT
<213> ORGANISM: Homo sapiens

<400> SEQUENCE: 52

Met Asp Met Arg Val Pro Ala Gln Leu Gly Leu Leu Leu Leu Trp
1                   5                  10                  15

Leu Arg Gly Ala Arg Cys Glu Val Gln Leu Val Gln Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Asp Leu Leu Asp Tyr Asp Leu Leu
        115                 120                 125

Thr Gly Tyr Gly Tyr Trp Gly Gln Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255
```

Pro Val Ala Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
        290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 53
<211> LENGTH: 235
<212> TYPE: PRT
<213> ORGANISM: Homo sapiens

<400> SEQUENCE: 53

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Gly
        35                  40                  45

Ile Ser Arg Ser Tyr Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Ser Ser Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe

```
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
                210                 215                 220

Pro Val Thr Lys Ser Phe Asn Arg Gly Glu Cys
225                 230                 235

<210> SEQ ID NO 54
<211> LENGTH: 471
<212> TYPE: PRT
<213> ORGANISM: Homo sapiens

<400> SEQUENCE: 54

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Pro Ser Gln Thr Leu Ser Leu Thr Cys Thr Val Ser Gly Gly Ser Ile
                35                  40                  45

Ser Ser Gly Asp Tyr Phe Trp Ser Trp Ile Arg Gln Leu Pro Gly Lys
                50                  55                  60

Gly Leu Glu Trp Ile Gly His Ile His Asn Ser Gly Thr Thr Tyr Tyr
65                  70                  75                  80

Asn Pro Ser Leu Lys Ser Arg Val Thr Ile Ser Val Asp Thr Ser Lys
                85                  90                  95

Lys Gln Phe Ser Leu Arg Leu Ser Ser Val Thr Ala Ala Asp Thr Ala
                100                 105                 110

Val Tyr Tyr Cys Ala Arg Asp Arg Gly Gly Asp Tyr Tyr Tyr Gly Met
                115                 120                 125

Asp Val Trp Gly Gln Gly Thr Thr Val Thr Val Ser Ser Ala Ser Thr
                130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
                210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285
```

```
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 55
<211> LENGTH: 236
<212> TYPE: PRT
<213> ORGANISM: Homo sapiens

<400> SEQUENCE: 55

Met Asp Met Arg Val Pro Ala Gln Leu Leu Gly Leu Leu Leu Leu Trp
1               5                   10                  15
Leu Ser Gly Ala Arg Cys Asp Ile Gln Met Thr Gln Ser Pro Ser Ser
            20                  25                  30
Leu Ser Ala Ser Val Gly Asp Arg Val Thr Ile Thr Cys Gln Ala Ser
        35                  40                  45
Gln Asp Ile Ser Asn Tyr Leu Asn Trp Tyr Gln Gln Lys Pro Gly Lys
    50                  55                  60
Ala Pro Lys Leu Leu Ile Tyr Asp Ala Ser Asn Leu Glu Thr Gly Val
65                  70                  75                  80
Pro Ser Arg Phe Ser Gly Ser Gly Ser Gly Thr Asp Phe Thr Phe Thr
                85                  90                  95
Ile Ser Ser Leu Gln Pro Glu Asp Ile Ala Thr Tyr Phe Cys Gln His
            100                 105                 110
Phe Asp His Leu Pro Leu Ala Phe Gly Gly Gly Thr Lys Val Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
```

```
Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 56
<211> LENGTH: 464
<212> TYPE: PRT
<213> ORGANISM: Homo sapiens

<400> SEQUENCE: 56

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Ser Ser Gly Asp Tyr Tyr Trp Thr Trp Ile Arg Gln Ser Pro Gly Lys
    50                  55                  60

Gly Leu Glu Trp Ile Gly His Ile Tyr Tyr Ser Gly Asn Thr Asn Tyr
65                  70                  75                  80

Asn Pro Ser Leu Lys Ser Arg Leu Thr Ile Ser Ile Asp Thr Ser Lys
                85                  90                  95

Thr Gln Phe Ser Leu Lys Leu Ser Ser Val Thr Ala Ala Asp Thr Ala
            100                 105                 110

Ile Tyr Tyr Cys Val Arg Asp Arg Val Thr Gly Ala Phe Asp Ile Trp
        115                 120                 125

Gly Gln Gly Thr Met Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
```

```
                        325                 330                 335
Lys Cys Lys Val Ser Asn Lys Gly Leu Pro Ala Pro Ile Glu Lys Thr
                340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
                450                 455                 460

<210> SEQ ID NO 57
<211> LENGTH: 236
<212> TYPE: PRT
<213> ORGANISM: Homo sapiens

<400> SEQUENCE: 57

Met Glu Thr Pro Ala Gln Leu Leu Phe Leu Leu Leu Leu Trp Leu Pro
1               5                   10                  15

Asp Thr Ala Ser Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
        35                  40                  45

Val Ser Asn Ser Tyr Leu Ala Trp Tyr Gln Gln Lys Pro Gly Gln Ala
    50                  55                  60

Pro Arg Leu Leu Ile Tyr Gly Ala Ser Ser Arg Ala Pro Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp His Ser Ala Gly Trp Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 58
<211> LENGTH: 460
<212> TYPE: PRT
<213> ORGANISM: Homo sapiens

<400> SEQUENCE: 58

```
Met Gly Ser Thr Ala Ile Leu Gly Leu Leu Ala Val Leu Gln Gly
1               5                   10                  15

Val Ala Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Arg Asn Ala Met Phe Trp Val Arg Gln Ala Pro Gly Lys Gly Leu
50                  55                  60

Glu Trp Val Ser Gly Ile Gly Thr Gly Gly Ala Thr Ser Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Arg Tyr Tyr Phe Pro Trp Trp Gly Gln Gly Thr
            115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Asn Phe Gly Thr Gln Thr Tyr Thr Cys Asn Val Asp His Lys Pro Ser
210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
            275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
370                 375                 380
```

```
Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
        420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
        450                 455                 460
```

<210> SEQ ID NO 59
<211> LENGTH: 234
<212> TYPE: PRT
<213> ORGANISM: Homo sapiens

<400> SEQUENCE: 59

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Arg Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Arg Tyr
            100                 105                 110

Gly Ser Ser His Thr Phe Gly Gln Gly Thr Lys Leu Glu Ile Ser Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 60
<211> LENGTH: 467
<212> TYPE: PRT
<213> ORGANISM: Homo sapiens

<400> SEQUENCE: 60

```
Met Gly Ser Thr Ala Ile Leu Ala Leu Leu Leu Ala Val Leu Gln Gly
1               5                   10                  15
```

```
Val Cys Ala Glu Val Gln Leu Val Gln Ser Gly Ala Glu Val Lys Lys
            20                  25                  30

Pro Gly Glu Ser Leu Lys Ile Ser Cys Lys Val Ser Gly Tyr Phe Phe
            35                  40                  45

Thr Thr Tyr Trp Ile Gly Trp Val Arg Gln Met Pro Gly Lys Gly Leu
 50                      55                  60

Glu Tyr Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Gly Gly Asn Trp Asn Cys Phe Asp Tyr Trp Gly
            115                 120                 125

Gln Gly Thr Leu Val Thr Val Ser Ser Ala Ser Thr Lys Gly Pro Ser
130                     135                 140

Val Phe Pro Leu Ala Pro Ser Ser Lys Ser Thr Ser Gly Gly Thr Ala
145                     150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Arg Val Glu Pro Lys Ser Cys
225                     230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                     295                 300

His Asn Ala Lys Thr Lys Pro Arg Glu Glu Gln Tyr Asn Ser Thr Tyr
305                     310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                     390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430
```

```
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
    450                 455                 460
Pro Gly Lys
465
```

<210> SEQ ID NO 61
<211> LENGTH: 241
<212> TYPE: PRT
<213> ORGANISM: Homo sapiens

<400> SEQUENCE: 61

```
Met Asp Met Arg Val Pro Ala Gln Leu Leu Gly Leu Leu Leu Leu Trp
1               5                   10                  15
Leu Arg Gly Ala Arg Cys Asp Val Val Met Thr Gln Ser Pro Leu Ser
                20                  25                  30
Leu Pro Val Thr Pro Gly Glu Pro Ala Ser Ile Ser Cys Arg Ser Ser
            35                  40                  45
Gln Ser Leu Leu His Ser Asn Gly Tyr Asn Tyr Leu Asp Trp Tyr Leu
    50                  55                  60
Gln Lys Pro Gly Gln Ser Pro Gln Leu Leu Ile Tyr Leu Gly Ser Asn
65                  70                  75                  80
Arg Ala Ser Gly Val Pro Asp Arg Phe Ser Gly Ser Gly Ser Gly Thr
                85                  90                  95
Asp Phe Thr Leu Lys Ile Ser Arg Val Glu Ala Glu Asp Val Gly Val
            100                 105                 110
Tyr Tyr Cys Met Gln Gly Thr His Trp Pro Leu Thr Phe Gly Gln Gly
    115                 120                 125
Thr Lys Val Glu Ile Lys Arg Thr Val Ala Ala Pro Ser Val Phe Ile
130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
Gln Asp Ser Lys Asp Ser Thr Tyr Ser Leu Ser Ser Thr Leu Thr Leu
    195                 200                 205
Ser Lys Ala Asp Tyr Glu Lys His Lys Val Tyr Ala Cys Glu Val Thr
210                 215                 220
His Gln Gly Leu Ser Ser Pro Val Thr Lys Ser Phe Asn Arg Gly Glu
225                 230                 235                 240
Cys
```

<210> SEQ ID NO 62
<211> LENGTH: 471
<212> TYPE: PRT
<213> ORGANISM: Homo sapiens

<400> SEQUENCE: 62

```
Met Asp Met Arg Val Pro Ala Gln Leu Leu Gly Leu Leu Leu Leu Trp
1               5                   10                  15
Leu Arg Gly Ala Arg Cys Gln Val Gln Leu Gln Glu Ser Gly Pro Gly
                20                  25                  30
Leu Val Lys Pro Ser Gly Thr Leu Ser Leu Thr Cys Ala Val Ser Gly
```

-continued

```
                35                  40                  45
Gly Ser Ile Ser Ser Asn Trp Trp Ser Trp Val Arg Gln Pro Pro
 50                  55                  60
Gly Lys Gly Leu Glu Trp Ile Gly Glu Ile Tyr His Ser Gly Ser Thr
 65                  70                  75                  80
Asn Tyr Asn Pro Ser Leu Lys Ser Arg Val Thr Ile Ser Val Asp Lys
                 85                  90                  95
Ser Lys Asn Gln Phe Ser Leu Lys Leu Ser Ser Val Thr Ala Ala Asp
                100                 105                 110
Thr Ala Val Tyr Tyr Cys Ala Arg Trp Thr Gly Arg Thr Asp Ala Phe
                115                 120                 125
Asp Ile Trp Gly Gln Gly Thr Met Val Thr Val Ser Ser Ala Ser Thr
    130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
                195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
    275                 280                 285
Asp Val Ser His Glu Asp Pro Glu Val Lys Phe Asn Trp Tyr Val Asp
290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
                355                 360                 365
Glu Pro Gln Val Tyr Thr Leu Pro Pro Ser Arg Asp Glu Leu Thr Lys
                370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Lys Leu Thr Val Asp Lys Ser Arg Trp Gln Gln Gly Asn Val Phe Ser
                435                 440                 445
Cys Ser Val Met His Glu Ala Leu His Asn His Tyr Thr Gln Lys Ser
450                 455                 460
```

```
Leu Ser Leu Ser Pro Gly Lys
465                 470

<210> SEQ ID NO 63
<211> LENGTH: 234
<212> TYPE: PRT
<213> ORGANISM: Homo sapiens

<400> SEQUENCE: 63

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Phe Gln Gln Lys Pro Gly Gln Ala Pro
    50                  55                  60

Arg Pro Leu Ile Tyr Asp Ala Ser Thr Arg Ala Thr Gly Val Pro Ala
65                  70                  75                  80

Arg Phe Ser Gly Ser Gly Ser Gly Thr Asp Phe Thr Leu Thr Ile Ser
                85                  90                  95

Ser Leu Gln Ser Glu Asp Phe Ala Val Tyr Tyr Cys Gln Gln Tyr Asp
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 64
<211> LENGTH: 461
<212> TYPE: PRT
<213> ORGANISM: Homo sapiens

<400> SEQUENCE: 64

Met Glu Trp Thr Trp Arg Val Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Arg Tyr Gly Ile Ser Trp Val Arg Gln Ala Pro Gly Gln Gly Leu
    50                  55                  60

Glu Trp Met Gly Trp Ile Ser Thr Tyr Ser Gly Asn Thr Asn Tyr Ala
65                  70                  75                  80
```

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Arg Gln Leu Tyr Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 239
<212> TYPE: PRT
<213> ORGANISM: Homo sapiens

<400> SEQUENCE: 65

Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Gly Gln Ser
        35                  40                  45

Leu Leu His Ser Asp Gly Lys Thr Tyr Leu Tyr Trp Tyr Leu Gln Lys
    50                  55                  60

Pro Gly Gln Pro Pro Gln Phe Leu Ile Tyr Glu Val Ser Asn Arg Phe
65                  70                  75                  80

Ser Arg Val Pro Asp Arg Phe Ser Gly Ser Gly Ser Gly Thr Asp Phe
                85                  90                  95

Thr Leu Arg Ile Ser Arg Val Glu Ala Glu Asp Val Gly Ile Tyr Tyr
            100                 105                 110

Cys Met Gln Ser Ile Gln Leu Pro Trp Thr Phe Gly Gln Gly Thr Gln
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 66
<211> LENGTH: 459
<212> TYPE: PRT
<213> ORGANISM: Homo sapiens

<400> SEQUENCE: 66

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Gly Tyr Gly Met His Trp Val Arg Gln Ala Pro Gly Lys Gly Leu
    50                  55                  60

Glu Trp Val Ala Val Ile Ser Tyr Asp Gly Asn Asp Lys Tyr Tyr Ala
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Leu Arg Val Leu Trp Gly Gln Gly Thr Leu
        115                 120                 125

-continued

Val Thr Val Ser Ser Ala Ser Thr Lys Gly Pro Ser Val Phe Pro Leu
            130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Asn
        195                 200                 205

Phe Gly Thr Gln Thr Tyr Thr Cys Asn Val Asp His Lys Pro Ser Asn
210                 215                 220

Thr Lys Val Asp Lys Thr Val Glu Arg Lys Cys Cys Val Glu Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Gln Phe Asn
            275                 280                 285

Trp Tyr Val Asp Gly Val Glu Val His Asn Ala Lys Thr Lys Pro Arg
290                 295                 300

Glu Glu Gln Phe Asn Ser Thr Phe Arg Val Val Ser Val Leu Thr Val
305                 310                 315                 320

Val His Gln Asp Trp Leu Asn Gly Lys Glu Tyr Lys Cys Lys Val Ser
                325                 330                 335

Asn Lys Gly Leu Pro Ala Pro Ile Glu Lys Thr Ile Ser Lys Thr Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Met Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 67
<211> LENGTH: 235
<212> TYPE: PRT
<213> ORGANISM: Homo sapiens

<400> SEQUENCE: 67

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Ser Tyr Leu Asn Trp Tyr Gln Gln Lys Pro Gly Lys
 50                  55                  60

Ala Pro Lys Leu Leu Ile Tyr Ser Thr Ser Arg Leu Asn Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Asp Ile Lys His Pro Thr Phe Gly Gln Gly Thr Lys Val Glu Ile Lys
                115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 68
<211> LENGTH: 465
<212> TYPE: PRT
<213> ORGANISM: Homo sapiens

<400> SEQUENCE: 68

Met Asp Trp Thr Trp Arg Ile Leu Phe Leu Val Ala Ala Thr Gly
1                5                  10                  15

Ala His Ser Glu Val Gln Leu Val Gln Ser Gly Ala Glu Val Lys Lys
                 20                  25                  30

Pro Gly Ser Ser Val Lys Val Ser Cys Lys Ala Ser Gly Phe Thr Phe
                 35                  40                  45

Thr Asp Tyr Ile Met His Trp Val Arg Gln Ala Pro Gly Gln Gly Leu
 50                  55                  60

Glu Trp Met Gly Tyr Ile Asn Pro Tyr Asn Asp Asp Thr Glu Tyr Asn
 65                  70                  75                  80

Glu Lys Phe Lys Gly Arg Val Thr Ile Thr Ala Asp Lys Ser Thr Ser
                 85                  90                  95

Thr Ala Tyr Met Glu Leu Ser Ser Leu Arg Ser Glu Asp Thr Ala Val
                100                 105                 110

Tyr Tyr Cys Ala Arg Ser Ile Tyr Tyr Asp Ala Pro Phe Ala Tyr
                115                 120                 125

Trp Gly Gln Gly Thr Leu Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe

```
                180             185                 190
Pro Ala Val Leu Gln Ser Ser Gly Leu Tyr Ser Leu Ser Val Val
            195                 200                 205

Thr Val Pro Ser Ser Asn Phe Gly Thr Gln Thr Tyr Thr Cys Asn Val
            210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Gln Phe Asn Trp Tyr Val Asp Gly Val Glu Val His Asn
            290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

Lys
465

<210> SEQ ID NO 69
<211> LENGTH: 233
<212> TYPE: PRT
<213> ORGANISM: Homo sapiens

<400> SEQUENCE: 69

Met Gly Ser Thr Ala Ile Leu Gly Leu Leu Leu Ala Val Leu Gln Gly
1               5                   10                  15

Gly Arg Ala Ser Tyr Val Leu Thr Gln Pro Pro Ser Val Ser Val Ala
            20                  25                  30

Pro Gly Gln Thr Ala Arg Ile Thr Cys Gly Gly Asn Asn Leu Gly Ser
        35                  40                  45

Lys Ser Val His Trp Tyr Gln Gln Lys Pro Gly Gln Ala Pro Val Leu
    50                  55                  60

Val Val Tyr Asp Asp Ser Asp Arg Pro Ser Trp Ile Pro Glu Arg Phe
65                  70                  75                  80
```

```
Ser Gly Ser Asn Ser Gly Asn Thr Ala Thr Leu Thr Ile Ser Arg Gly
                85                  90                  95

Glu Ala Gly Asp Glu Ala Asp Tyr Tyr Cys Gln Val Trp Asp Ser Ser
            100                 105                 110

Ser Asp His Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 70
<211> LENGTH: 467
<212> TYPE: PRT
<213> ORGANISM: Homo sapiens

<400> SEQUENCE: 70

Met Gly Ser Thr Ala Ile Leu Gly Leu Leu Leu Ala Val Leu Gln Gly
1               5                   10                  15

Gly Arg Ala Gln Met Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Arg Thr Tyr Gly Met His Trp Val Arg Gln Ala Pro Gly Lys Gly Leu
    50                  55                  60

Glu Trp Val Ala Val Ile Trp Tyr Asp Gly Ser Asn Lys His Tyr Ala
65                  70                  75                  80

Asp Ser Val Lys Gly Arg Phe Thr Ile Thr Arg Asp Asn Ser Lys Asn
                85                  90                  95

Thr Leu Asn Leu Gln Met Asn Ser Leu Arg Ala Glu Asp Thr Ala Val
            100                 105                 110

Tyr Tyr Cys Ala Arg Ala Pro Gln Trp Glu Leu Val His Glu Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220
```

```
Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 71
<211> LENGTH: 234
<212> TYPE: PRT
<213> ORGANISM: Homo sapiens

<400> SEQUENCE: 71

Met Gly Val Pro Thr His Leu Leu Gly Leu Leu Leu Leu Trp Ile Thr
1               5                   10                  15

His Ala Ile Cys Asp Ile Arg Met Thr Gln Ser Pro Ala Ser Leu Ser
            20                  25                  30

Ala Ser Leu Gly Glu Thr Val Asn Ile Glu Cys Leu Ala Ser Glu Asp
        35                  40                  45

Ile Tyr Ser Asp Leu Ala Trp Tyr Gln Gln Lys Pro Gly Lys Ser Pro
    50                  55                  60

Gln Leu Leu Ile Tyr Asn Ala Asn Ser Leu Gln Asn Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Thr Tyr Phe Cys Gln Gln Tyr Asn
            100                 105                 110

Asn Tyr Pro Pro Thr Phe Gly Gly Gly Thr Lys Leu Glu Leu Lys Arg
```

```
                    115                 120                 125
Ala Asp Ala Ala Pro Thr Val Ser Ile Phe Pro Pro Ser Thr Glu Gln
            130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                    165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
                195                 200                 205

His Asn Leu Tyr Thr Cys Glu Val Val His Lys Thr Ser Ser Ser Pro
            210                 215                 220

Val Val Lys Ser Phe Asn Arg Asn Glu Cys
225                 230

<210> SEQ ID NO 72
<211> LENGTH: 465
<212> TYPE: PRT
<213> ORGANISM: Homo sapiens

<400> SEQUENCE: 72

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
                20                  25                  30

Pro Ala Asn Ser Leu Lys Leu Ser Cys Ala Ala Ser Gly Phe Thr Phe
            35                  40                  45

Ser Asp Tyr Ala Met Ala Trp Val Arg Gln Ser Pro Lys Lys Gly Leu
        50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr Gly Leu Gly Ile Ala Thr Asp Tyr Phe Asp Tyr
        115                 120                 125

Trp Gly Gln Gly Val Leu Val Thr Val Ser Ser Ala Glu Thr Thr Ala
130                 135                 140

Pro Ser Val Tyr Pro Leu Ala Pro Gly Thr Ala Leu Lys Ser Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ala Leu Ser Ser Gly Val His Thr Phe
            180                 185                 190

Pro Ala Val Leu Gln Ser Gly Leu Tyr Thr Leu Thr Ser Ser Val Thr
        195                 200                 205

Val Pro Ser Ser Thr Trp Pro Ser Gln Thr Val Thr Cys Asn Val Ala
    210                 215                 220

His Pro Ala Ser Ser Thr Lys Val Asp Lys Lys Ile Val Pro Arg Asn
225                 230                 235                 240

Cys Gly Gly Asp Cys Lys Pro Cys Ile Cys Thr Gly Ser Glu Val Ser
                245                 250                 255
```

```
Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Gln Asp Asp
        275                 280                 285

Pro Glu Val His Phe Ser Trp Phe Val Asp Asp Val Glu Val His Thr
    290                 295                 300

Ala Gln Thr Arg Pro Pro Glu Glu Gln Phe Asn Ser Thr Phe Arg Ser
305                 310                 315                 320

Val Ser Glu Leu Pro Ile Leu His Gln Asp Trp Leu Asn Gly Arg Thr
                325                 330                 335

Phe Arg Cys Lys Val Thr Ser Ala Ala Phe Pro Ser Pro Ile Glu Lys
            340                 345                 350

Thr Ile Ser Lys Pro Glu Gly Arg Thr Gln Val Pro His Val Tyr Thr
        355                 360                 365

Met Ser Pro Thr Lys Glu Glu Met Thr Gln Asn Glu Val Ser Ile Thr
    370                 375                 380

Cys Met Val Lys Gly Phe Tyr Pro Pro Asp Ile Tyr Val Glu Trp Gln
385                 390                 395                 400

Met Asn Gly Gln Pro Gln Glu Asn Tyr Lys Asn Thr Pro Pro Thr Met
                405                 410                 415

Asp Thr Asp Gly Ser Tyr Phe Leu Tyr Ser Lys Leu Asn Val Lys Lys
            420                 425                 430

Glu Lys Trp Gln Gln Gly Asn Thr Phe Thr Cys Ser Val Leu His Glu
        435                 440                 445

Gly Leu His Asn His His Thr Glu Lys Ser Leu Ser His Ser Pro Gly
    450                 455                 460

Lys
465

<210> SEQ ID NO 73
<211> LENGTH: 237
<212> TYPE: PRT
<213> ORGANISM: Homo sapiens

<400> SEQUENCE: 73

Met Asp Met Arg Val Pro Ala Gln Leu Leu Gly Leu Leu Leu Leu Trp
1               5                   10                  15

Leu Arg Gly Ala Arg Cys Glu Ser Ala Leu Thr Gln Pro Ala Ser Val
            20                  25                  30

Ser Gly Ser Pro Gly Gln Ser Ile Thr Ile Ser Cys Thr Gly Thr Ser
        35                  40                  45

Ser Asp Val Gly Gly Tyr Asn Ser Val Ser Trp Tyr Gln Gln His Pro
    50                  55                  60

Gly Lys Ala Pro Lys Leu Met Ile Tyr Glu Val Ser Asn Arg Pro Ser
65                  70                  75                  80

Gly Val Ser Asn Arg Phe Ser Gly Ser Lys Ser Gly Asn Thr Ala Ser
                85                  90                  95

Leu Thr Ile Ser Gly Leu Gln Ala Glu Asp Glu Ala Asp Tyr Tyr Cys
            100                 105                 110

Asn Ser Tyr Thr Ser Thr Ser Met Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160
```

```
Ile Ser Asp Phe Tyr Pro Gly Ala Val Thr Val Ala Trp Lys Ala Asp
                165                 170                 175
Ser Ser Pro Val Lys Ala Gly Val Glu Thr Thr Thr Pro Ser Lys Gln
            180                 185                 190
Ser Asn Asn Lys Tyr Ala Ala Ser Ser Tyr Leu Ser Leu Thr Pro Glu
        195                 200                 205
Gln Trp Lys Ser His Arg Ser Tyr Ser Cys Gln Val Thr His Glu Gly
    210                 215                 220
Ser Thr Val Glu Lys Thr Val Ala Pro Thr Glu Cys Ser
225                 230                 235

<210> SEQ ID NO 74
<211> LENGTH: 460
<212> TYPE: PRT
<213> ORGANISM: Homo sapiens

<400> SEQUENCE: 74

Met Asp Trp Thr Trp Arg Ile Leu Phe Leu Val Ala Ala Ala Thr Gly
1               5                   10                  15
Val His Ser Glu Val Gln Leu Val Gln Ser Gly Ala Glu Val Lys Lys
            20                  25                  30
Pro Gly Ala Ser Val Lys Val Ser Cys Lys Ala Ser Gly Tyr Thr Leu
        35                  40                  45
Thr Ser Tyr Gly Ile Ser Trp Val Arg Gln Ala Pro Gly Gln Gly Leu
    50                  55                  60
Glu Trp Met Gly Trp Val Ser Phe Tyr Asn Gly Asn Thr Asn Tyr Ala
65                  70                  75                  80
Gln Lys Leu Gln Gly Arg Gly Thr Met Thr Thr Asp Pro Ser Thr Ser
                85                  90                  95
Thr Ala Tyr Met Glu Leu Arg Ser Leu Arg Ser Asp Asp Thr Ala Val
            100                 105                 110
Tyr Tyr Cys Ala Arg Gly Tyr Gly Met Asp Val Trp Gly Gln Gly Thr
        115                 120                 125
Thr Val Thr Val Ser Ser Ala Ser Thr Lys Gly Pro Ser Val Phe Pro
    130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Asn Phe Gly Thr Gln Thr Tyr Thr Cys Asn Val Asp His Lys Pro Ser
    210                 215                 220
Asn Thr Lys Val Asp Lys Thr Val Glu Arg Lys Cys Cys Val Glu Cys
225                 230                 235                 240
Pro Pro Cys Pro Ala Pro Val Ala Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Gln Phe
            275                 280                 285
Asn Trp Tyr Val Asp Gly Val Glu Val His Asn Ala Lys Thr Lys Pro
```

```
                290             295             300
Arg Glu Glu Gln Phe Asn Ser Thr Phe Arg Val Val Ser Val Leu Thr
305                 310             315                 320

Val Val His Gln Asp Trp Leu Asn Gly Lys Glu Tyr Lys Cys Lys Val
                325             330             335

Ser Asn Lys Gly Leu Pro Ala Pro Ile Glu Lys Thr Ile Ser Lys Thr
            340             345             350

Lys Gly Gln Pro Arg Glu Pro Gln Val Tyr Thr Leu Pro Pro Ser Arg
            355             360             365

Glu Glu Met Thr Lys Asn Gln Val Ser Leu Thr Cys Leu Val Lys Gly
            370             375             380

Phe Tyr Pro Ser Asp Ile Ala Val Glu Trp Glu Ser Asn Gly Gln Pro
385             390             395                 400

Glu Asn Asn Tyr Lys Thr Thr Pro Pro Met Leu Asp Ser Asp Gly Ser
                405             410             415

Phe Phe Leu Tyr Ser Lys Leu Thr Val Asp Lys Ser Arg Trp Gln Gln
                420             425             430

Gly Asn Val Phe Ser Cys Ser Val Met His Glu Ala Leu His Asn His
            435             440             445

Tyr Thr Gln Lys Ser Leu Ser Leu Ser Pro Gly Lys
            450             455             460

<210> SEQ ID NO 75
<211> LENGTH: 234
<212> TYPE: PRT
<213> ORGANISM: Homo sapiens

<400> SEQUENCE: 75

Met Glu Thr Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
                20                  25                  30

Val Ser Pro Gly Glu Arg Ala Thr Leu Ser Cys Arg Ala Ser Gln Ser
            35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ala Thr Arg Ala Thr Gly Ile Pro Ala
65                  70                  75                  80

Arg Val Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
                100                 105                 110

Asn Trp Pro Leu Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205
```

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 76
<211> LENGTH: 472
<212> TYPE: PRT
<213> ORGANISM: Homo sapiens

<400> SEQUENCE: 76

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Asn Tyr Gly Met His Val Arg Gln Ala Pro Gly
    50                  55                  60

Glu Gly Leu Glu Trp Val Ala Ala Ile Trp Phe Asp Ala Ser Asp Lys
65              70                  75                  80

Tyr Tyr Ala Asp Ala Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Gln Ala Ile Phe Gly Val Val
        115                 120                 125

Pro Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Cys Glu Glu Gln
305                 310                 315                 320

Tyr Gly Ser Thr Tyr Arg Cys Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Lys
465                 470

<210> SEQ ID NO 77
<211> LENGTH: 231
<212> TYPE: PRT
<213> ORGANISM: Homo sapiens

<400> SEQUENCE: 77

Met Ala Trp Ile Pro Leu Phe Leu Gly Val Leu Ala Tyr Cys Thr Gly
1               5                   10                  15

Ser Val Ala Ser Tyr Glu Val Thr Gln Ala Pro Ser Val Ser Val Ser
            20                  25                  30

Pro Gly Gln Thr Ala Ser Ile Thr Cys Ser Gly Asp Lys Leu Gly Asp
        35                  40                  45

Lys Tyr Ala Cys Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
            85                  90                  95

Gln Ala Met Asp Glu Ala Asp Tyr Tyr Cys Gln Ala Trp Asp Ser Ser
            100                 105                 110

Thr Ala Val Phe Gly Gly Gly Thr Lys Leu Thr Val Leu Gly Gln Pro
            115                 120                 125

Lys Ala Ala Pro Ser Val Thr Leu Phe Pro Pro Ser Ser Glu Glu Leu
130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
            165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
            195                 200                 205

Ser Tyr Ser Cys Gln Val Thr His Glu Gly Ser Thr Val Glu Lys Thr
            210                 215                 220

Val Ala Pro Thr Glu Cys Ser
225                 230

<210> SEQ ID NO 78
<211> LENGTH: 467
<212> TYPE: PRT
<213> ORGANISM: Homo sapiens

<400> SEQUENCE: 78

Met Asp Trp Thr Trp Ser Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Gly Leu Ser Trp Val Arg Gln Ala Pro Gly Gln Gly Leu
    50                  55                  60

Glu Trp Met Gly Trp Ile Ile Pro Tyr Asn Gly Asn Thr Asn Ser Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Phe Cys Ala Arg Asp Arg Asp Tyr Gly Val Asn Tyr Asp Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 79
<211> LENGTH: 235
<212> TYPE: PRT
<213> ORGANISM: Homo sapiens

<400> SEQUENCE: 79

Met Ala Trp Ala Pro Leu Leu Thr Leu Leu Ala His Cys Thr Gly
1               5                   10                  15

Ser Trp Ala Asn Phe Met Leu Thr Gln Pro His Ser Val Ser Glu Ser
                20                  25                  30

Pro Gly Lys Thr Val Ala Ile Ser Cys Thr Arg Asn Ser Gly Ser Ile
            35                  40                  45

Ala Ser Asn Ser Val Gln Trp Tyr Gln Arg Pro Gly Ser Ser Pro
    50                  55                  60

Thr Thr Val Ile Phe Glu Asp Asn Gln Arg Pro Ser Gly Val Pro Asp
65                  70                  75                  80

Arg Phe Ser Gly Ser Ile Asp Ser Ser Ser Asn Ser Ala Ser Leu Thr
                85                  90                  95

Ile Ser Gly Leu Lys Thr Glu Asp Glu Ala Asp Tyr Tyr Cys Gln Ser
            100                 105                 110

Tyr Asp Ser Asn Asn Trp Val Phe Gly Gly Gly Thr Lys Leu Thr Val
        115                 120                 125

Leu Gly Gln Pro Lys Ala Asn Pro Thr Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 80
<211> LENGTH: 470
<212> TYPE: PRT
<213> ORGANISM: Homo sapiens

<400> SEQUENCE: 80
```

-continued

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Val Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Tyr Asp Tyr Gly Glu Asp Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
```

```
                   420                 425                 430
Leu Thr Val Asp Lys Ser Arg Trp Gln Gln Gly Asn Val Phe Ser Cys
                435                 440                 445
Ser Val Met His Glu Ala Leu His Asn His Tyr Thr Gln Lys Ser Leu
            450                 455                 460
Ser Leu Ser Pro Gly Lys
465                 470
```

<210> SEQ ID NO 81
<211> LENGTH: 236
<212> TYPE: PRT
<213> ORGANISM: Homo sapiens

<400> SEQUENCE: 81

```
Met Asp Met Arg Val Pro Ala Gln Leu Leu Gly Leu Leu Leu Leu Trp
1               5                  10                  15
Leu Arg Gly Ala Arg Cys Asp Ile Gln Met Thr Gln Ser Pro Ser Ser
                20                  25                  30
Leu Ser Ala Ser Val Gly Asp Arg Val Thr Ile Thr Cys Arg Ala Ser
            35                  40                  45
Gln Asp Ile Ser Asn Tyr Leu Asn Trp Tyr Gln Lys Pro Gly Lys
50                  55                  60
Ala Pro Lys Leu Leu Ile Tyr Tyr Thr Ser Arg Leu Leu Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Gly Asp Thr Leu Pro Tyr Thr Phe Gly Gly Gly Thr Lys Val Glu Ile
        115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
210                 215                 220
Ser Pro Val Thr Lys Ser Phe Asn Arg Gly Glu Cys
225                 230                 235
```

<210> SEQ ID NO 82
<211> LENGTH: 468
<212> TYPE: PRT
<213> ORGANISM: Homo sapiens

<400> SEQUENCE: 82

```
Met Asp Trp Thr Trp Arg Ile Leu Phe Leu Val Ala Ala Thr Gly
1               5                  10                  15
Ala His Ser Glu Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
```

```
                35                  40                  45
Thr Asp Tyr Asn Met His Trp Val Arg Gln Ala Pro Gly Gln Gly Leu
 50                  55                  60
Glu Trp Met Gly Glu Ile Asn Pro Asn Ser Gly Ala Gly Tyr Asn
 65                  70                  75                  80
Gln Lys Phe Lys Gly Arg Val Thr Met Thr Asp Thr Ser Thr Ser
                 85                  90                  95
Thr Ala Tyr Met Glu Leu Arg Ser Leu Arg Ser Asp Thr Ala Val
                100                 105                 110
Tyr Tyr Cys Ala Arg Leu Gly Tyr Asp Asp Ile Tyr Asp Asp Trp Tyr
                115                 120                 125
Phe Asp Val Trp Gly Gln Gly Thr Thr Val Thr Val Ser Ser Ala Ser
130                 135                 140
Thr Lys Gly Pro Ser Val Phe Pro Leu Ala Pro Cys Ser Arg Ser Thr
145                 150                 155                 160
Ser Glu Ser Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
                195                 200                 205
Ser Val Val Thr Val Pro Ser Ser Asn Phe Gly Thr Gln Thr Tyr Thr
210                 215                 220
Cys Asn Val Asp His Lys Pro Ser Asn Thr Lys Val Asp Lys Thr Val
225                 230                 235                 240
Glu Arg Lys Cys Cys Val Glu Cys Pro Pro Cys Pro Ala Pro Pro Val
                245                 250                 255
Ala Gly Pro Ser Val Phe Leu Phe Pro Pro Lys Pro Lys Asp Thr Leu
                260                 265                 270
Met Ile Ser Arg Thr Pro Glu Val Thr Cys Val Val Val Asp Val Ser
                275                 280                 285
His Glu Asp Pro Glu Val Gln Phe Asn Trp Tyr Val Asp Gly Val Glu
                290                 295                 300
Val His Asn Ala Lys Thr Lys Pro Arg Glu Glu Gln Phe Asn Ser Thr
305                 310                 315                 320
Phe Arg Val Val Ser Val Leu Thr Val Val His Gln Asp Trp Leu Asn
                325                 330                 335
Gly Lys Glu Tyr Lys Cys Lys Val Ser Asn Lys Gly Leu Pro Ala Pro
                340                 345                 350
Ile Glu Lys Thr Ile Ser Lys Thr Lys Gly Gln Pro Arg Glu Pro Gln
                355                 360                 365
Val Tyr Thr Leu Pro Pro Ser Arg Glu Glu Met Thr Lys Asn Gln Val
                370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Met Leu Asp Ser Asp Gly Ser Phe Phe Leu Tyr Ser Lys Leu Thr
                420                 425                 430
Val Asp Lys Ser Arg Trp Gln Gln Gly Asn Val Phe Ser Cys Ser Val
                435                 440                 445
Met His Glu Ala Leu His Asn His Tyr Thr Gln Lys Ser Leu Ser Leu
450                 455                 460
```

Ser Pro Gly Lys
465

<210> SEQ ID NO 83
<211> LENGTH: 240
<212> TYPE: PRT
<213> ORGANISM: Homo sapiens

<400> SEQUENCE: 83

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Asp Ser Ser Asp Asn Lys Asn Tyr Leu Ala Trp Tyr Gln Gln
    50                  55                  60

Lys Pro Gly Gln Pro Pro Lys Leu Leu Ile Tyr Trp Ala Ser Asn Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Asp Pro Phe Thr Phe Gly Pro Gly Thr
        115                 120                 125

Lys Val Asp Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 84
<211> LENGTH: 465
<212> TYPE: PRT
<213> ORGANISM: Homo sapiens

<400> SEQUENCE: 84

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

```
Gln Lys Leu Gln Gly Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Glu Ser Trp Phe Gly Glu Val Phe Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 85
<211> LENGTH: 236
```

```
<212> TYPE: PRT
<213> ORGANISM: Homo sapiens

<400> SEQUENCE: 85

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Gly Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Asn Tyr Tyr Cys Gln Gln
            100                 105                 110

Ala Asn Ser Phe Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 86
<211> LENGTH: 466
<212> TYPE: PRT
<213> ORGANISM: Homo sapiens

<400> SEQUENCE: 86

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Val Ser Gly
        35                  40                  45

Tyr Thr Leu Ser Asp Leu Ser Ile His Trp Val Arg Gln Ala Pro Gly
    50                  55                  60

Lys Gly Leu Glu Trp Met Gly Gly Phe Asp Pro Gln Asp Gly Glu Thr
65                  70                  75                  80

Ile Tyr Ala Gln Lys Phe Gln Gly Arg Val Thr Met Thr Glu Asp Thr
                85                  90                  95

Ser Thr Asp Thr Ala Tyr Met Glu Leu Ser Ser Leu Lys Ser Glu Asp
            100                 105                 110
```

-continued

```
Thr Ala Val Tyr Tyr Cys Ala Thr Gly Ser Ser Ser Trp Phe Asp
            115                 120             125

Pro Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
    275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465
```